(12) United States Patent
Craighead et al.

(10) Patent No.: US 10,040,047 B2
(45) Date of Patent: Aug. 7, 2018

(54) DEVICE FOR RECOVERY AND ISOLATION OF BIOMOLECULES

(71) Applicant: CORNELL UNIVERSITY, Ithaca, NY (US)

(72) Inventors: Harold Craighead, Ithaca, NY (US); Christine Tan, Singapore (SG)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/735,874

(22) Filed: Jun. 10, 2015

(65) Prior Publication Data

US 2015/0360195 A1   Dec. 17, 2015

Related U.S. Application Data

(63) Continuation of application No. 13/641,206, filed as application No. PCT/US2011/032491 on Apr. 14, 2011, now abandoned.

(60) Provisional application No. 61/324,214, filed on Apr. 14, 2010.

(51) Int. Cl.
| | |
|---|---|
| *B01J 19/00* | (2006.01) |
| *G01N 33/543* | (2006.01) |
| *C12N 15/10* | (2006.01) |
| *G01N 33/53* | (2006.01) |

(52) U.S. Cl.
CPC ...... *B01J 19/0046* (2013.01); *C12N 15/1048* (2013.01); *G01N 33/5308* (2013.01); *G01N 33/54386* (2013.01); *B01J 2219/00585* (2013.01); *B01J 2219/00596* (2013.01); *B01J 2219/00722* (2013.01)

(58) Field of Classification Search
None
See application file for complete search history.

(56) References Cited

U.S. PATENT DOCUMENTS

| | | | | |
|---|---|---|---|---|
| 5,783,759 | A  * | 7/1998 | Wielinger | B01L 3/5023 73/864.72 |
| 6,627,226 | B2 * | 9/2003 | Burgoyne | C12N 15/1006 424/443 |
| 2007/0105087 | A1 * | 5/2007 | Ban | G01N 33/5082 435/4 |
| 2013/0004967 | A1 * | 1/2013 | Halverson | B01L 3/50853 435/7.8 |

* cited by examiner

*Primary Examiner* — Betty J Forman
(74) *Attorney, Agent, or Firm* — FisherBroyles, LLP; Andrew K. Gonsalves, Esq.

(57) ABSTRACT

The present invention relates to a device for isolating and recovering a biomolecule from a test sample. The device includes a support and at least one peelable layer deposited on at least a portion of the support. The peelable layer includes a substrate having a target component immobilized on the substrate. The device is effective for isolating and recovering a biomolecule having affinity to the target component. The present invention also relates to systems and methods of using the device. The present invention also relates to a biomolecule elution strip and related methods.

21 Claims, 21 Drawing Sheets

1. Test sample containing different types of biomolecules
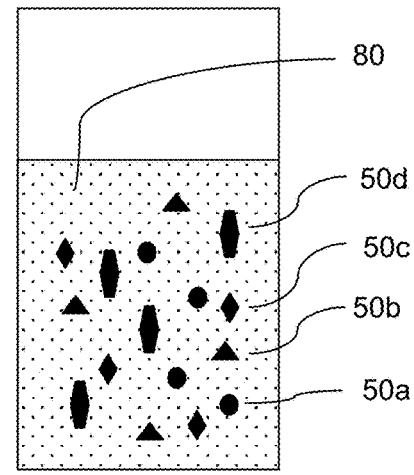
2. Device with certain types of biomolecules selectively bound to the target component after contacting test sample to device
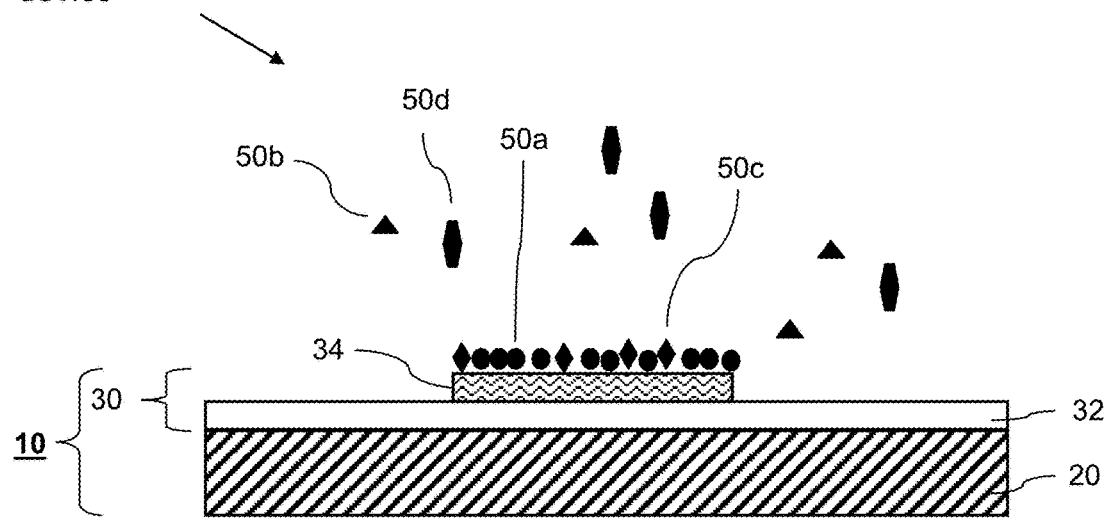
FIG. 2F 3. Peelable layer containing the biomolecules bound to the target component after removal of peelable layer from the support.
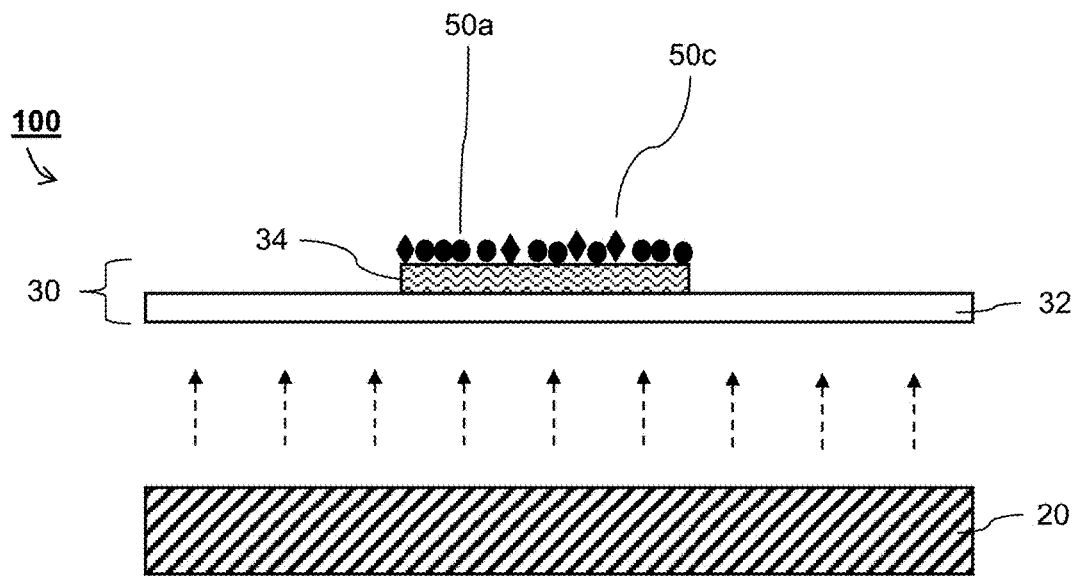
4. Biomolecules after elution from target component of peelable layer.
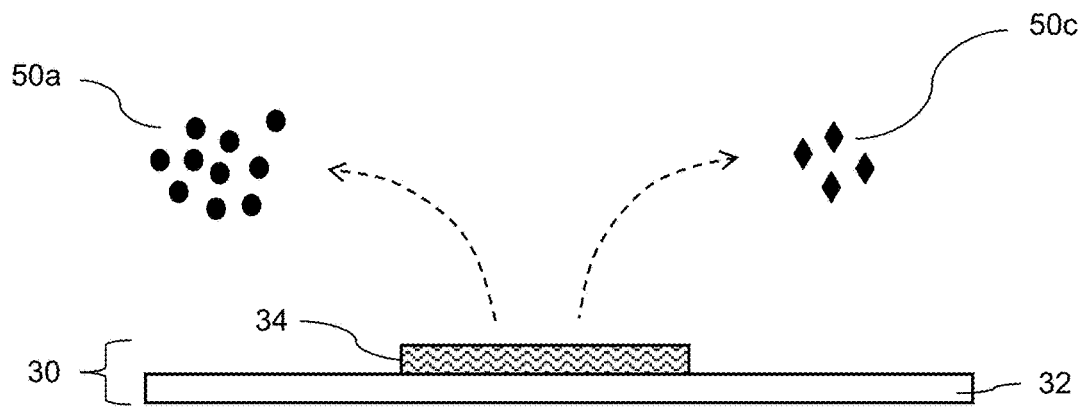
*FIG. 2F (continued)*

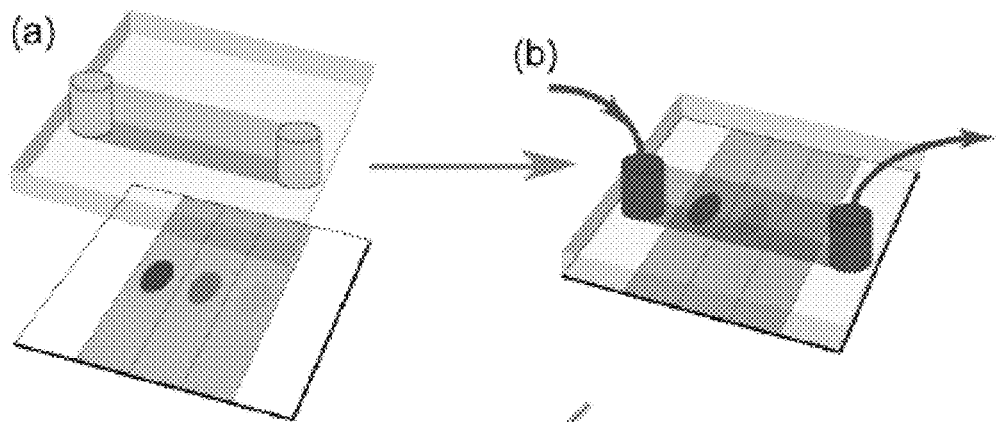
Figure 8A  Figure 8B
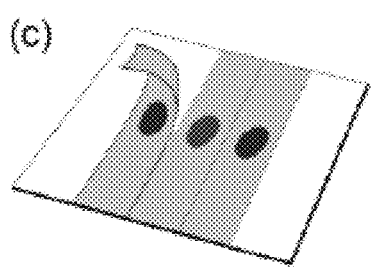 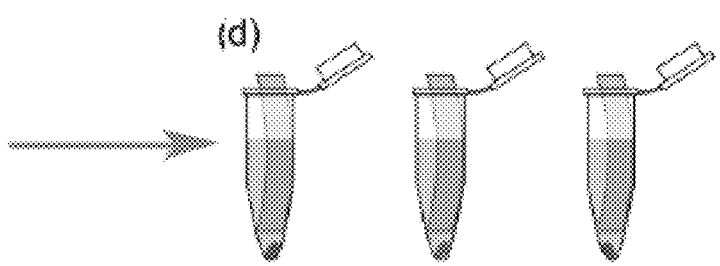
Figure 8C  Figure 8D

| Name | Sequence (5'→3') | Bases |
|---|---|---|
| AlexaFluor 488 thrombin aptamer | *AlexaFluor488*-TTTTTTTTTTTTGGTTGGTGTGGTTGG (SEQ ID NO:1) | 27 |
| AlexaFluor 594 PDGF-BB aptamer | *AlexaFluor594*-TTTTTTTTTTTTTACTCAGGGCACTGCAAGCAATTGTGGTCCCAATGGGCTGAGTAT (SEQ ID NO:2) | 57 |
| AlexaFluor 647 VEGF aptamer | *AlexaFluor647*-TTTTTTTTTTTTCCCGTCTTCCAGACAAGAGTGCAGGGG (SEQ ID NO:3) | 39 |
| Thrombin template | *phos*-AGGACACGCATTTTACTAGATAGCTAGCTTTCGATCGTTCTGAGCAGACAACG (SEQ ID NO:4) | 53 |
| Thrombin aptamer-primer | GGTTGGTGTGGTTGGTTTTTTTTAATGCGTGTCCTCGTTGTCTGCTC (SEQ ID NO:5) | 48 |
| PDGF-BB template | *phos*-TAGCACGGACATATATGATGGTACCGCAGTATGAGTATCTCCTATCACTACTAAGTGGAAGAAATGTAACTGTTTCCTTC (SEQ ID NO:6) | 80 |
| PDGF-BB aptamer-primer | TACTCAGGGCACTGCAAGCAATTGTGGTCCCAATGGGCTGAGTATTTTTTTTGTCCGTGCTAGAAGGAAACAGTTAC (SEQ ID NO:7) | 77 |
| DNA Library | GGGAGAATTCAACTGCCATCTAGGC-N$_{60}$-GTACTACAAGCTTCTGGACTCGGT (SEQ ID NO:8) | 109 |
| Libfwd | GGGAGAATTCAACTGCCATCTAGGC (SEQ ID NO:9) | 25 |
| Librev1 | ACCGAGTCCAGAAGCTTGTAGTAC (SEQ ID NO:10) | 24 |
| Librev2 | *phos*-ACCGAGTCCAGAAGCTTGTAGTAC (SEQ ID NO:11) | 24 |

*FIG. 9*

DEVICE FOR RECOVERY AND ISOLATION OF BIOMOLECULES

CROSS-REFERENCE TO RELATED APPLICATIONS

This application is a continuation of U.S. patent application Ser. No. 13/641,206, filed Oct. 15, 2012, which is a U.S. National Phase filing under 35 U.S.C. § 371 of International Application No. PCT/US2011/032491, filed Apr. 14, 2011, and published as WO 2011/130511-A2 on Oct. 20, 2011, which claims benefit of priority from U.S. Provisional Patent Application Ser. No. 61/324,214, filed Apr. 14, 2010. The entire contents of each of the prior applications are incorporated herein by reference in their entirety.

GOVERNMENT RIGHTS STATEMENT

This invention was made with Government support under grant number 1R01DC007489-01A1 awarded by the National Institutes of Health. The Government has certain rights in the invention.

FIELD OF THE INVENTION

The present invention relates to a device for, inter alia, isolating and recovering a biomolecule from a test sample. The present invention also relates to systems and methods of using the device.

BACKGROUND OF THE INVENTION

Multiplexed affinity-based screening is widespread in biology, whereby potential biomolecular candidates in a sample pool are screened against capturing biomolecules immobilized on an array surface. For example, DNA microarrays enable the massively parallel screening of sample RNA that may hybridize to any of thousands of gene sequences arrayed on a surface. It is often useful to recover the bound biomolecule species afterwards for complete identification (e.g. DNA sequencing) and to generate more copies (e.g. PCR amplification), particularly if the original sample pool is a priori unknown. One such instance is the identification of previously uncharacterized corona viruses such as SARS, whereby viral nucleic acids hybridized to a DNA microarray were individually scraped off using tungsten needles for PCR [1]. Although this approach is simple, its disadvantages include contamination, loss and destruction of samples.

Current technologies fail to combine both multiplexed affinity-based screening and sample recovery. Whatman's FTA® Elute have been used to recover total DNA without specificity from whole blood or buccal cheek cells [2-5]. HPLC systems allow for affinity-based screening and sample recovery, but multiple columns and the systems can be prohibitively expensive. Microfluidic systems have had some early success at addressing these problems. For example, nucleic acid aptamers that showed binding to protein have been selected from a sample library pool and recovered using heating electrodes [6] or micromagnetic beads [7]. The challenge remains to reliably isolate and individually recover biomolecule species of interest after multiplexed screening.

Aptamers are short length nucleic acids that bind to proteins, and are emerging as potential therapeutic molecules that could target proteins involved in disease. Systematic evolution of ligands by exponential enrichment (SELEX) is a process utilized to select aptamers with high affinity binding to proteins. SELEX requires both affinity-based screening and subsequent recovery of aptamers that bind to proteins for PCR amplification. With each cycle of SELEX, the stringency of binding in the screening process is increased, and at the end of several SELEX rounds, aptamers with high binding affinity are systematically evolved. SELEX is time consuming and microfluidics have been shown to shorten the process [7-9]. However these microfluidic systems involve selection against one protein at a time; it would be desirable to develop a microfluidic system or other technologies capable of multiplexed selection and screening simultaneously.

The present invention is directed to overcoming these and other deficiencies in the art.

SUMMARY OF THE INVENTION

In one aspect, the present invention relates to a device for isolating and recovering a biomolecule from a test sample. The device includes a support and at least one peelable layer deposited on at least a portion of the support. The peelable layer includes a substrate having a target component immobilized on the substrate. The target component is a target biomolecule and/or a target biomaterial. The device is effective for isolating and recovering a biomolecule having affinity to the target component. As used herein, in various embodiments, the term "peel-strip" is meant to refer to a peelable layer of the present invention.

In one embodiment, the device can further include a release coating deposited between the support and peelable layer. The release coating is effective to facilitate separation of the peelable layer from the support.

In another embodiment, the device can further include a biomolecule bound with affinity to the target component.

In another aspect, the present invention relates to a system for isolating and recovering a biomolecule having affinity to a target component. The system includes a device of the present invention and a test sample delivery module effective to control delivery of a test sample in fluid form to the peelable layer of the device, thereby enabling a biomolecule contained in the test sample to bind to the target component if the biomolecule has affinity to the target component.

In another aspect, the present invention relates to a method for making a device for isolating and recovering a biomolecule having affinity to a target component. This method involves: (i) providing a support; (ii) depositing a substrate onto the support, where the substrate is effective to immobilize a target component thereon; and (iii) immobilizing the target component on the substrate under conditions effective to yield at least one peelable layer that includes the substrate having the target component immobilized thereon. The target component can be a target biomolecule and/or a target biomaterial. Further, the at least one peelable layer is removably secured to the support.

In one embodiment, this method further involves depositing a release coating between the support and peelable layer. The release coating is effective to facilitate separation of the peelable layer from the support.

In another embodiment, this method further involves depositing a secondary mechanical support layer between the support and the at least one peelable layer. The secondary mechanical support layer is effective to facilitate removal of the peelable layer from the support.

In yet another embodiment, the step of depositing at least one substrate onto at least a portion of the support further includes separating the substrate into independently removable substrate strips prior to immobilizing the target component thereon, thereby yielding a plurality of peelable layers that are independently removable from the support.

In another aspect, the present invention relates to a method of isolating and recovering a sample biomolecule having affinity to a target component. This method involves: (i) providing a device of the present invention; (ii) contacting a test sample to the at least one peelable layer under conditions effective to allow a sample biomolecule having affinity to the target component to bind to the target component, thereby isolating the sample biomolecule from the test sample; (iii) separating the peelable layer containing the isolated sample biomolecule from the support; and (iv) eluting the isolated sample biomolecule from the peelable layer.

In another aspect, the present invention relates to a method for multiplexed screening of a test sample for the presence of a sample biomolecule having affinity to a target component. This method involves: (i) providing a device of the present invention, where the device includes a plurality of peelable layers, with each peelable layer having a different target component immobilized thereon; (ii) contacting a test sample to the plurality of peelable layers under conditions effective to allow a sample biomolecule contained in the test sample to bind to the different target components, if the sample biomolecule has affinity to the target component; and (iii) detecting binding of the sample biomolecule to one or more of the different target components.

In one embodiment, this method further involves: (i) separating the peelable layer containing the isolated sample biomolecule from the support; and (ii) eluting the isolated sample biomolecule from the peelable layer.

In another aspect, the present invention relates to a method of preparing a biomolecule elution strip for storage and recovery of a sample biomolecule having affinity to a target component. This method involves: (i) providing a device of the present invention; (ii) contacting a test sample to the peelable layer of the device under conditions effective to removably bind a sample biomolecule contained in the test sample to the target component, if said sample biomolecule has affinity to the target component; and (iii) removing the peelable layer from the support to yield a biomolecule elution strip. The biomolecule elution strip prepared by this method includes a sample biomolecule removably bound to the target component of the peelable layer.

In another aspect, the present invention relates to a biomolecule elution strip produced according to the methods of the present invention.

The device, systems, and methods of the present invention provide numerous advantages over the existing art, including, for example: (i) the ability to combine multiplexed affinity-based screening and individual sample recovery; (ii) highly simplified sample recovery by peeling off each Peel-Strip without specialized equipment; and (iii) preservation of sample integrity. The present invention also can be used along with large scale formats (e.g., 96-well formats) with many broad applications for recovering a diversity of affinity-captured biomolecules and cells in a compact and easy-to-use system.

Other advantages of the present invention over the prior art include, without limitation, the following: (i) the ability to store captured bound sample biomolecules in individual strips, allowing for a sample biomolecule to be eluted (released) and recovered at a later time; (ii) the ability to coat any surface (e.g., support surface) with parylene (substrate); and (iii) the ability to confer surface functional groups independently of the surface in order to yield a device suitable for the applications described herein.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIGS. 2A-2F are schematic drawings of various illustrative embodiments of the device of the present invention and the methods of using the device to isolate and elute biomolecules having affinity to the target component contained on the device of the present invention. The embodiments are shown in either side or cross-sectional views.

FIGS. 8A-8F are schematics and photographs of various embodiments of the device and process of the present invention. FIGS. 8A-8D are schematics showing integration of Peel-Strips with microfluidics, and the process for separating and recovering aptamers. FIG. 8E is a photograph of a device—the assembled Peel-Strips with microfluidics. FIG. 8F is a photograph showing recovery of bound aptamers as the strip is placed into an eluting buffer inside a microcentrifuge tube. Buffer is shown here for illustrative purpose, and does not represent the actual volume used.

FIG. 9 is a table showing sequences of DNA used in peel-strip recovery experiments for aptamers.

DETAILED DESCRIPTION OF THE INVENTION

The present invention relates to devices, systems, and methods that enable the efficient isolation, identification, storage, and recovery of biomolecules from test samples. The present invention enables numerous applications that involve multiplexed affinity-based screening of biomolecules having potential therapeutic or other biologically important activity. For example, the present invention can be used in applications that include, but are not limited to, the following: systematic evolution of ligands by exponential enrichment (SELEX); drug screening; and capturing cells of a certain attribute from a mixture (e.g., selecting rare pluripotent stem cells from blood for therapeutic purposes, or capturing rare circulating tumor cells (CTCs) from body fluids for diagnostics/early detection).

As set forth herein, in one aspect, the present invention relates to a device for isolating and recovering a biomolecule from a test sample. The device includes a support and at least one peelable layer deposited on at least a portion of the support. The peelable layer includes a substrate having a target component immobilized on the substrate. The target component is a target biomolecule and/or a target biomaterial. As noted herein, the device is effective for, inter alia, isolating and recovering a biomolecule having affinity to the target component. In one embodiment, the device can further include a release coating deposited between the support and peelable layer. The release coating is effective to facilitate separation of the peelable layer from the support. In another embodiment, the device can further include a biomolecule bound with affinity to the target component.

FIGS. 1A-1H are schematic drawings of illustrative embodiments and aspects of the device of the present invention. In order to further describe the device of the present invention, reference is made to various figures, as discussed herein below.

Figure 1A:
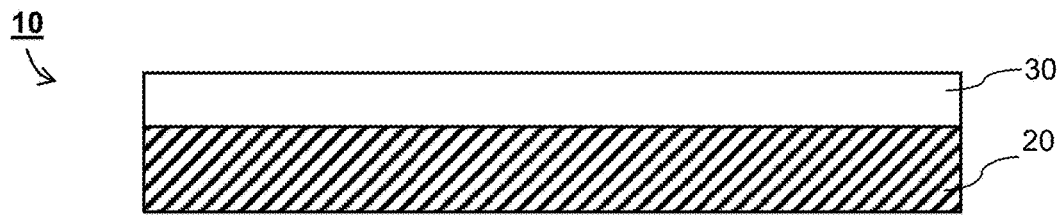
FIGS. 1A-1H are schematic drawings of various illustrative embodiments of the device of the present invention. The embodiments are shown in either side or cross-sectional views.

As shown in FIG. 1A, device 10 includes support 20 and at least one peelable layer 30 deposited on at least a portion of support 20. While FIG. 1A shows peelable layer 30 deposited on the entire surface of support 20, the present invention contemplates that peelable layer 30 can also be deposited on only a portion of support 20. Further, as discussed in more detail herein, multiple, independently removable peelable layers can be deposited on the surface of a single support. These multiple peelable layers are not layered on top of one another, but are deposited on a single support and separated by a boundary that allows each peelable layer to be removed from the same support independently of one another.

Figure 1B:
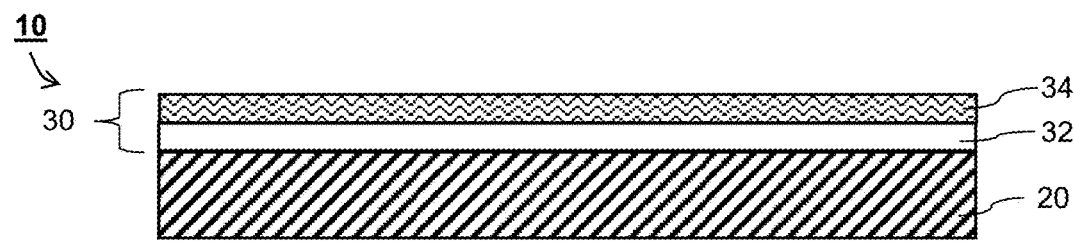
Figure 1C:
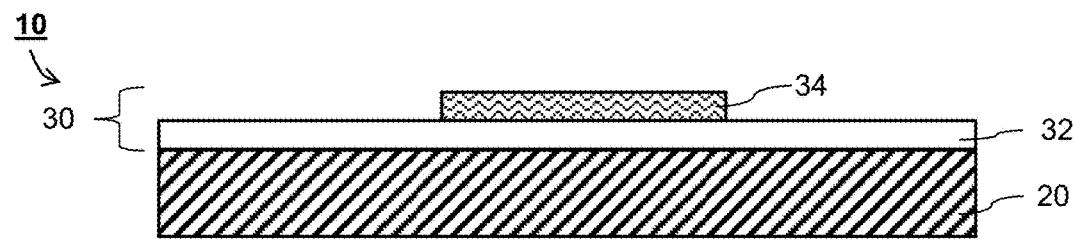

As shown in FIGS. 1B and 1C, peelable layer 30 includes substrate 32 having target component 34 immobilized on substrate 32, with substrate 32 deposited between support 20 and target component 34. While FIG. 1B shows target component 34 deposited on the entire surface of substrate 32, the present invention contemplates that target component 34 need not be deposited over the entire surface of substrate 32. Thus, as shown in FIG. 1C, target component 34 can be deposited on a portion of substrate 32. This can be achieved in various ways, including, for example, by spot applying target component 34 to substrate 32 so that target component 34 is contained on just a portion (e.g., as a spot) of substrate 32.

Support 20 can be made of any material suitable for providing a platform onto which peelable layer 30 can be deposited and then subsequently removed (i.e., peelable layer 30 and support 20 are made of materials that allow for peelable layer 30 to be removed, e.g., peeled off, from support 20). For example, a suitable support can be made of such materials as silicon, polystyrene, polypropylene, glass, ceramic, plastic, polyethylene, polyvinylidene, and the like. Other suitable materials for use as the support are well known by those of ordinary skill in the art. The support can be configured in various forms, including, for example, as a wafer (e.g., silicon), microscope slide (e.g., glass), microtiter plate (e.g., 96-well plate), and the like.

Substrate 32 can be any material having surface properties effective for immobilizing target component 34 thereto, with the surface properties being characterized by the presence of functional groups including, but not limited to, hydrophilic groups, hydrophobic groups, carboxyl groups, amine groups, gold groups, and the like. Examples of suitable substrate materials can include, without limitation, polymers, naturally occurring organic materials, and the like. Suitable polymers for use as the substrate can include, without limitation, a para-xylylene polymer (parylene), polymethylmethacrylate (PMMA), polydimethylsiloxane (PDMS), and the like. In a particular embodiment, the para-xylylene polymer can be parylene A or derivatives thereof (discussed in more detail below). A suitable naturally occurring organic material can be nitrocellulose. With respect to substrates made of nitrocellulose, spun-on dried films of nitrocellulose can be effective in that they can be used for DNA and protein adsorption, without requiring covalent linkages, and can be peeled off of the support. In another embodiment, the surface of substrate 32 can be modified by depositing a thin layer of gold on substrate 32, with the gold being effective for enabling thiol-gold linkages. Thus, in a particular embodiment, a thin gold layer can be deposited on top of the substrate layer (e.g., parylene A), allowing for thiol-biomolecules to be linked onto the substrate (e.g., parylene A). The present invention further contemplates the use of other suitable methods for depositing desired functional groups onto substrate 32. Such methods are well known in the art (see, e.g., Hermanson, Greg T., *Bioconjugate Techniques, Second Edition*, Academic Press, Inc., 2008, which is hereby incorporated by reference herein).

Substrate 32 can be deposited onto support 20 using various deposition techniques, including, for example, chemical vapor deposition (CVD) (e.g., for parylene substrates), spin coating (e.g., for nitrocellulose substrates), and the like.

As discussed herein, in one embodiment, substrate 32 can be a para-xylylene polymer (parylene). Parylene is a family of CVD deposited polymers used in engineering surfaces for biological applications [10], such as micropatterning [11, 12] or direct coating to create bioactive surfaces. Parylene films are biocompatible, chemically inert, conformal with high surface coverage uniformity, and able to withstand a variety of solvents without degradation or swelling. Further, parylene generally does not interfere with biology. While parylene is generally known and used as a stencil (with openings for patterning biomolecules), as discussed more fully herein, the present invention is unique in that it uses parylene as a substrate and mechanical support to directly immobilize biomolecules onto the parylene polymer.

Parylene C, which is commonly used, is effective to specifically peel-off to pattern cells down to nanoscale resolution etc. [A11, A12]. Parylene enables conformal coating that adds chemical functionality to nearly any surface [A13, A14] through the use of substituted precursor dimers. Chemically reactive parylene-A films containing substituted amine groups can be coated onto nearly any surface to confer new functional groups for covalent linkage of biomolecules or drugs [13-16]. This is an advantage over traditional surface chemistries, such as silanization or thiol self-assembly on gold, that require specialized surfaces to work. Thus, parylene A is useful because of the amine groups that allow covalent coupling with a plethora of functional groups.

While parylene peel-off (lift-off) has been used for nano- and micropatterning, the devices, systems, and methods of the present invention are the first to directly use parylene as a mechanical support for probing biomolecular interactions and then retrieving the affinity-captured biomolecule of interest using peel-off. Further, as set forth herein, in certain embodiments, the present invention further includes a simple microfluidic chip incorporating Peel-Strips (e.g., made of substrates such as parylene A) for the separation and recovery of multiple aptamers via an affinity-based array. In a particular embodiment, a parylene A layer is used as the substrate, thereby conferring chemical functionality to enable the immobilization of any protein/DNA, which allows a microarray format for parallel screening/capture of multiple biomolecular interactions, and thereafter enabling one to separate and recover the biomolecule species of interest. Further, in another particular embodiment, the Peel-Strips are incorporated into microfluidics for low reagent consumption, particularly for future use of precious library reagents (e.g., in SELEX). Therefore, the present invention includes advantages over the existing art in that it is easy-to-use, there is no need for specialized equipment (e.g., optics, electronics) to recover the samples, and it does not mechanically destroy a sample such as scraping the surface. The Peel-Strips of the present invention can be a convenient platform for cataloging/storage until ready to use, whereby the user will just peel off the strip to recover a biomolecule species.

Target component 34 of peelable layer 30 can be a target biomolecule and/or a target biomaterial. As used herein, the term "target biomolecule" refers to a protein, a peptide, a nucleic acid molecule (e.g., DNA), an aptamer, an oligonucleotide, a saccharide, a polysaccharide, a lipid, a glycolipid, a glycoprotein, a cell, and combinations thereof. As used herein, the term "target biomaterial" refers to a sol-gel, a hydrogel laden with proteins, a Matrigel, an artificially constructed scaffold with cells, and combinations thereof.

The target component is characterized in that it has binding affinity to a biomolecule (e.g., a biomolecule contained in a sample to be tested), where the biomolecule can be, for example, an aptamer, a protein, a peptide, a nucleic acid molecule, an oligonucleotide, a cell-associated molecule, a saccharide, a polysaccharide, a lipid, a glycolipid, a glycoprotein, a cell, and combinations thereof. Therefore, in one embodiment, the device can further include a biomolecule bound with affinity to the target component. Such an embodiment is described in more detail below and illustrated in FIGS. 1G and 1H.

The target component can be immobilized on the substrate by various immobilization interactions known in the art, including, without limitation, immobilization interactions involving covalent binding (e.g., covalent binding of amine groups on parylene A to amine groups on proteins via aldehyde chemistry), physical adsorption (e.g., DNA or proteins being physically adsorbed onto a nitrocellulose surface), and/or physical steric trapping (e.g., trapping of biomolecules inside porous scaffolds or hydrogels). The target component can be modified to include functional groups to facilitate immobilization of the target component to the substrate. Suitable functional groups can include, without limitation, hydrophilic groups, hydrophobic groups, carboxyl groups, amine groups, thiol groups, and the like. One of ordinary skill in the art can readily determine particular functional groups to use for a particular target component and sample biomolecule.

In a particular embodiment, the target component is effective to maintain its bioactivity or functionality, particularly prior to being contacted with a test sample containing or believed to contain a biomolecule having affinity to the target component.

Suitable target components can include, without limitation, target biomolecules and target biomaterials that are implicated in or play important roles in mammalian diseases or the regulation of cellular activity. Examples of attributes of such target components can include, without limitation, blood clotting, angiogenesis, permeability, tumor progression, regulation of endothelial cells, etc. Specific examples of suitable target components that are implicated in diseases can include, without limitation, human TNF-$\alpha$, human VEGF, human PDGF-BB, human PSA, human $\alpha$-Thrombin, and the like.

Figure 1D:
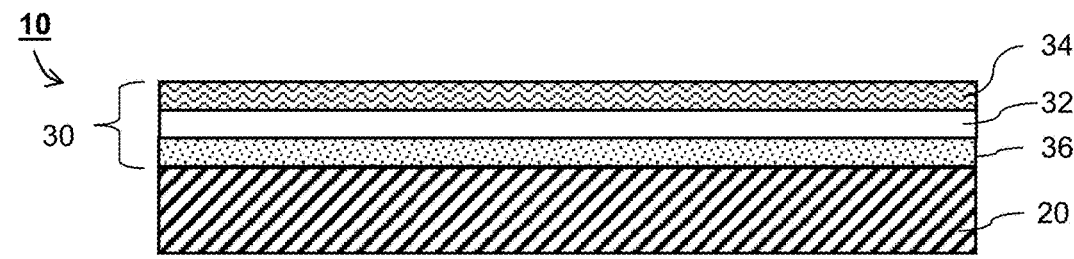
Figure 1E:
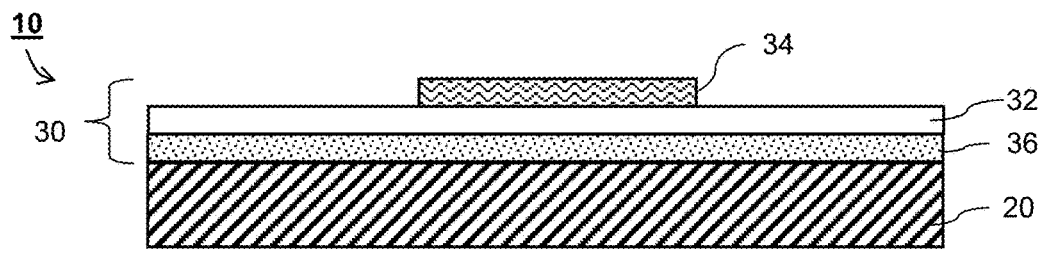

As shown in FIGS. 1D and 1E, in one embodiment, peelable layer 30 can further include secondary mechanical support layer 36, which is deposited between support 20 and substrate 32 of peelable layer 30. Secondary mechanical support layer 36 is effective to facilitate removal of peelable layer 30 from support 20. Therefore, in one embodiment, secondary mechanical support layer 36 is configured to be removable from support 20, but to remain connected to substrate 32. In one embodiment, the secondary mechanical support layer can be a layer of a para-xylylene polymer such as Parylene C, Parylene AM, Parylene D, Parylene N, Parylene F, and derivatives thereof. While FIG. 1D shows secondary mechanical support layer 36, substrate 32, and target component 34 deposited on the entire surface of the layer directly below each respective layer, the present invention contemplates that secondary mechanical support layer 36, substrate 32, and target component 34 need not be deposited over the entire surface of the layer directly below. For example, FIG. 1E shows target component 34 deposited on a portion of substrate 32.

Figure 1F:

As shown in FIG. 1F, in one embodiment, device 10 can further include release coating 40 deposited between support 20 and peelable layer 30. In a particular embodiment, release coating 40 is deposited on at least a portion of support 20 and at least a portion of the first layer of peelable layer 30 is deposited on at least a portion of release coating 40. As used herein, release coating 40 can be any material that is effective to facilitate separation of the peelable layer from the support. Suitable materials for use as the release coating are known in the art and can include, without limitation, a detergent/surfactant, bovine serum albumin, a thin metal layer, and the like.

Figure 1G:
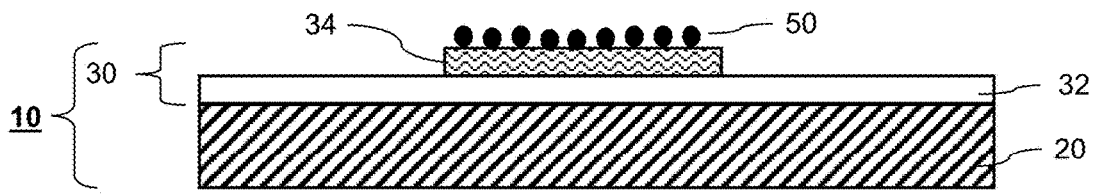

The present invention further includes a device having at least one biomolecule bound to the target component of the peelable layer, with the at least one biomolecule having binding affinity to the target component. Thus, as shown in FIG. 1G, in one embodiment, device 10 can further include biomolecule 50 bound with affinity to target component 34 of peelable layer 30. As set forth in more detail herein, the present invention also contemplates a device having a target component with more than one type of biomolecule bound thereto, thereby enabling affinity based screening and isolation of multiple and different types of biomolecules, where each type of biomolecule has a different binding affinity to the target component.

Figure 1H:
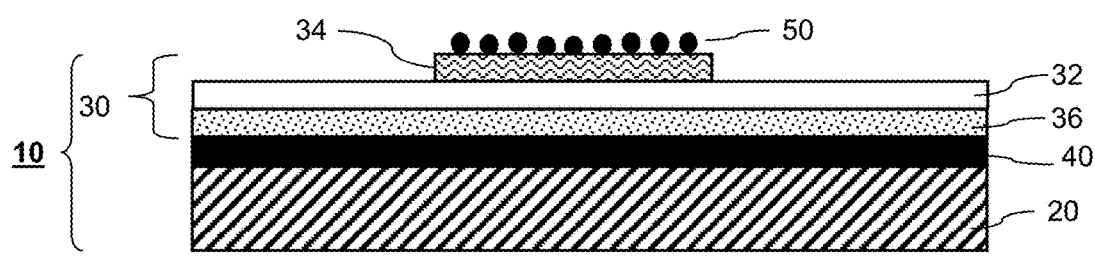

FIG. 1H is a schematic drawing showing all of the various components of the device of the present invention in a single drawing, and the general relationship of each component to one another. However, FIG. 1H is being provided for illustrative purposes only and is not intended to imply that all of the components shown in FIG. 1H are required for the device of the present invention to function. Further, while many of the components are shown to cover the entire layer upon which they are deposited, the present invention is not limited to requiring such a configuration, i.e., each component can be deposited on only a portion of the layer directly below.

As described herein, the device of the present invention is effective for isolating and recovering a biomolecule having affinity to the target component of the peelable layer. The device is also effective for multiplexed isolation and recovery of biomolecules from a test sample. The device can be designed to include a support that is configured to hold one peelable layer or a plurality of peelable layers. In embodiments configured to have a plurality of peelable layers, the device can be in the form of a microarray. The plurality of peelable layers can be configured to be independently removable from the support. In particular embodiments, the plurality of peelable layers are deposited on the support with each peelable layer having identical or different target components immobilized on the substrate of the peelable layer.

The peelable layer can be of any shape, including, for example, strips, squares, etc. In embodiments having a plurality of peelable layers, the peelable layers can be of the same or different shape. In these embodiments, the peelable layers can be of any shape, as long as each peelable layer can be individually isolated from one another, thereby enabling the removal of each individual peelable layer from the support.

The present invention also relates to a method for making a device for isolating and recovering a biomolecule having affinity to a target component. This method involves: (i) providing a support; (ii) depositing a substrate onto the support, where the substrate is effective to immobilize a target component thereon; and (iii) immobilizing the target component on the substrate under conditions effective to yield at least one peelable layer that includes the substrate having the target component immobilized thereon, with the at least one peelable layer being removably secured to the support.

The various components, materials, and techniques described herein above and below with respect to the device of the present invention maintain their meaning in the context of this method of making the device.

In one embodiment, this method further involves depositing a release coating between the support and peelable layer, with the release coating being effective to facilitate separation of the peelable layer from the support.

In another embodiment, this method further involves depositing a secondary mechanical support layer between the support and the at least one peelable layer, with the secondary mechanical support layer being effective to facilitate removal of the peelable layer from the support.

In yet another embodiment, the step of depositing at least one substrate onto at least a portion of the support further includes separating the substrate into independently removable substrate strips prior to immobilizing the target component thereon, thereby yielding a plurality of peelable layers that are independently removable from the support.

Separating the substrate into independently removable substrate strips can involve using techniques that include, but are not limited to, direct cutting, pre-defining perforation cutting, laser machining, photolithography patterning, and the like. Preparing a plurality of independently removable peelable layers on a support can be done by separating the substrate into independently removable substrate strips either before or after the target component is deposited onto the substrate.

The present invention also relates to a system for isolating and recovering a biomolecule having affinity to a target component. The system includes a device of the present invention and a test sample delivery module effective to control delivery of a test sample in fluid form to the peelable layer of the device, thereby enabling a biomolecule contained in the test sample to bind to the target component if the biomolecule has affinity to the target component.

The various components, materials, and techniques described herein above and below with respect to the device of the present invention maintain their meaning in the context of the system of the present invention.

In one embodiment, the test sample delivery module can be either a closed delivery system or an open delivery system.

As used herein, a "closed delivery system" refers to a delivery system that involves a microfluidic module or apparatus. For example, in one embodiment, the closed delivery system can be a microfluidic apparatus that includes (i) a chamber having a fluidic channel for introducing the test sample to the at least one peelable layer and (ii) a means for controlling flow of the test sample to the removable biomaterial layer. The chamber can be configured to include the following: (i) an inlet port at a first end of the fluidic channel of the chamber, said inlet port being for introducing the test sample to the peelable layer; and (ii) an outlet port at a second end of the fluidic channel of the chamber, said outlet port being for withdrawing the test sample from the peelable layer. In one embodiment, the means for controlling flow of the test sample to and from the peelable layer can be a peristaltic pump connected to the outlet port of the chamber.

As used herein, an "open delivery system" refers to a delivery system that uses an instrument effective to directly deliver a predetermined amount of a test sample fluid to the peelable layer. For example, the open delivery system can involve the use of an instrument such as a pipette to deliver the test sample to the peelable layer. In one embodiment, one or more pipettes can be configured for either manual or automated (e.g., robotic) delivery of the test sample to the peelable layer. Robotics can be used to automatically deliver the test sample to multiple, individually removable peelable layers on a single support (e.g., using a multi-well plate such as a 96-well plate).

The system of the present invention can further include a peeling mechanism for removing the peelable layer from the support. The peeling mechanism can involve manual or automated instruments suitable for removing the peeling layer from the support.

The system of the present invention can also further include a releasing mechanism for releasing the biomolecule from the peelable layer, after the peelable layer is removed from the support. The releasing mechanism can involve the use of elution buffers along with centrifugation and/or shaking instruments effective to facilitate removal of the biomolecule from the target component of the peelable layer.

The present invention also relates to a method of isolating and recovering a sample biomolecule having affinity to a target component. This method involves: (i) providing a device of the present invention; (ii) contacting a test sample to the at least one peelable layer under conditions effective to allow a sample biomolecule having affinity to the target component to bind to the target component, thereby isolating the sample biomolecule from the test sample; (iii) separating the peelable layer containing the isolated sample biomolecule from the support; and (iv) eluting the isolated sample biomolecule from the peelable layer.

The various components, materials, and techniques described herein above and below with respect to the device of the present invention maintain their meaning in the context of this method of using the device to isolate and recover a sample biomolecule having affinity to a target component.

The present invention also relates to a method for multiplexed screening of a test sample for the presence of a sample biomolecule having affinity to a target component. This method involves: (i) providing a device of the present invention, where the device includes a plurality of peelable layers, with each peelable layer having a different target component immobilized thereon; (ii) contacting a test sample to the plurality of peelable layers under conditions effective to allow a sample biomolecule contained in the test sample to bind to the different target components, if the sample biomolecule has affinity to the target component; and (iii) detecting binding of the sample biomolecule to one or more of the different target components.

The various components, materials, and techniques described herein above and below with respect to the device of the present invention maintain their meaning in the context of this method of using the device to isolate and recover a sample biomolecule having affinity to a target component.

In one embodiment, this method further involves: (i) separating the peelable layer containing the isolated sample biomolecule from the support; and (ii) eluting the isolated sample biomolecule from the peelable layer.

In one embodiment, the detecting step can involve detection techniques that include, but are not limited to, fluorescent immunostaining assays, bioactivity assays, fluorescence microscopy imaging assays, nucleic acid amplification assays (e.g., rolling circle amplification), and the like.

In another embodiment, the method can further involve: (i) separating the peelable layer containing the isolated sample biomolecule from the support; and (ii) eluting the isolated sample biomolecule from the peelable layer. Various separation and elution techniques, buffers, reagents, and instruments can be used, and are well known in the art.

The present invention also relates to a method of preparing a biomolecule elution strip for storage and recovery of a sample biomolecule having affinity to a target component. This method involves: (i) providing a device of the present invention; (ii) contacting a test sample to the peelable layer of the device under conditions effective to removably bind a sample biomolecule contained in the test sample to the target component, if said sample biomolecule has affinity to the target component; and (iii) removing the peelable layer from the support to yield a biomolecule elution strip. The biomolecule elution strip prepared by this method includes a sample biomolecule removably bound to the target component of the peelable layer. The present invention further relates to biomolecule elution strips prepared by this method.

The various components, materials, and techniques described herein above and below with respect to the device of the present invention maintain their meaning in the context of this method of preparing a biomolecule elution strip for storage and recovery of a sample biomolecule having affinity to a target component.

FIGS. 2A-2F and FIGS. 3A-3D are schematic drawings of illustrative embodiments and aspects of the devices, systems, and methods of the present invention, which devices, systems, and methods are described above and below. In order to further describe the devices, systems, and methods of the present invention, reference is made to these various figures, as discussed herein below. The below discussion of the figures is meant to supplement and correspond with other related disclosures contained herein with regard to the devices, systems, and methods of the present invention.

Figure 2A:
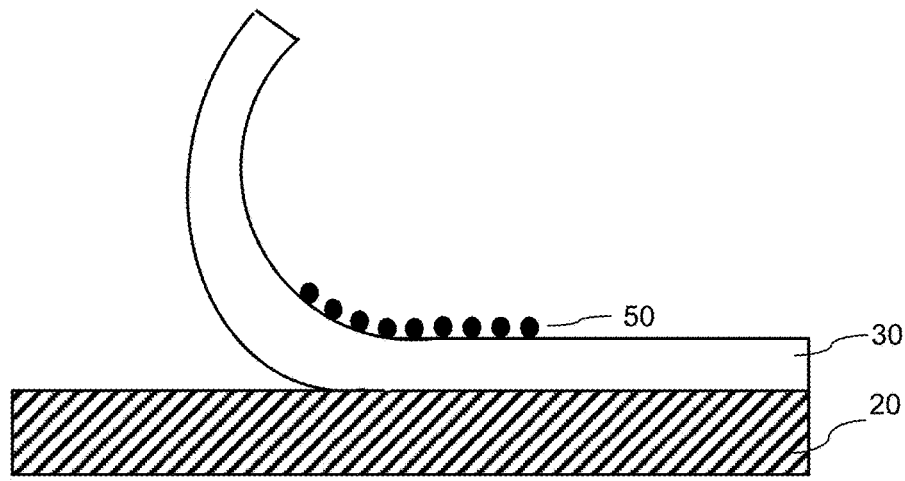

FIG. 2A illustrates a peelable layer being removed from a support, with a biomolecule bound with affinity to the peelable layer. As shown in FIG. 2A, peelable layer 30 can be removed (e.g., separated, peeled) from support 20, with biomolecules 50 being bound to a portion of peelable layer 30. Although not shown in FIG. 2A, as described elsewhere herein, peelable layer 30 includes a substrate having a target component deposited on the substrate. The target component is the portion of peelable layer 30 to which biomolecule 50 is bound (see FIG. 2C, discussed herein below). FIG. 2A shows the device after contacting it with a sample containing biomolecule 50.

Figure 2B:
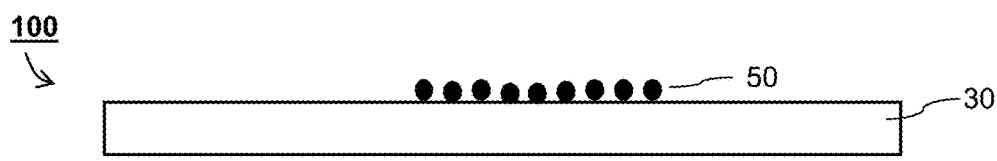
Figure 2C:
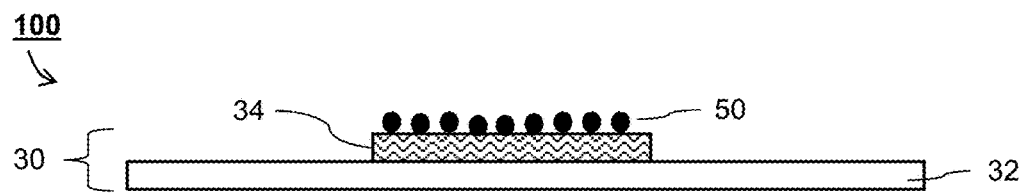

FIGS. 2B and 2C illustrate a peelable layer having biomolecules bound thereto, after the peelable layer has been removed from the support. As used herein, the term "biomolecule elution strip" refers to a peelable layer having at least one biomolecule bound with affinity to the target component of the peelable layer. FIG. 2B is a schematic of biomolecule elution strip 100. Biomolecule elution strip 100 includes peelable layer 30 having at least one biomolecule 50 bound with affinity thereto. While FIG. 2B does not expressly show biomolecules 50 bound to a target component, the present invention contemplates that biomolecules 50 are indeed bound to the target component with affinity. Thus, FIG. 2C is provided to illustrate biomolecule elution strip 100 having peelable layer 30 that includes substrate 32 and target component 34 deposited on substrate 32, with biomolecules 50 bound with affinity to target component 34. Biomolecule elution strip 100 can be stored for later elution of biomolecules 50 therefrom, enabling the various applications of use presented herein.

Figure 2D:
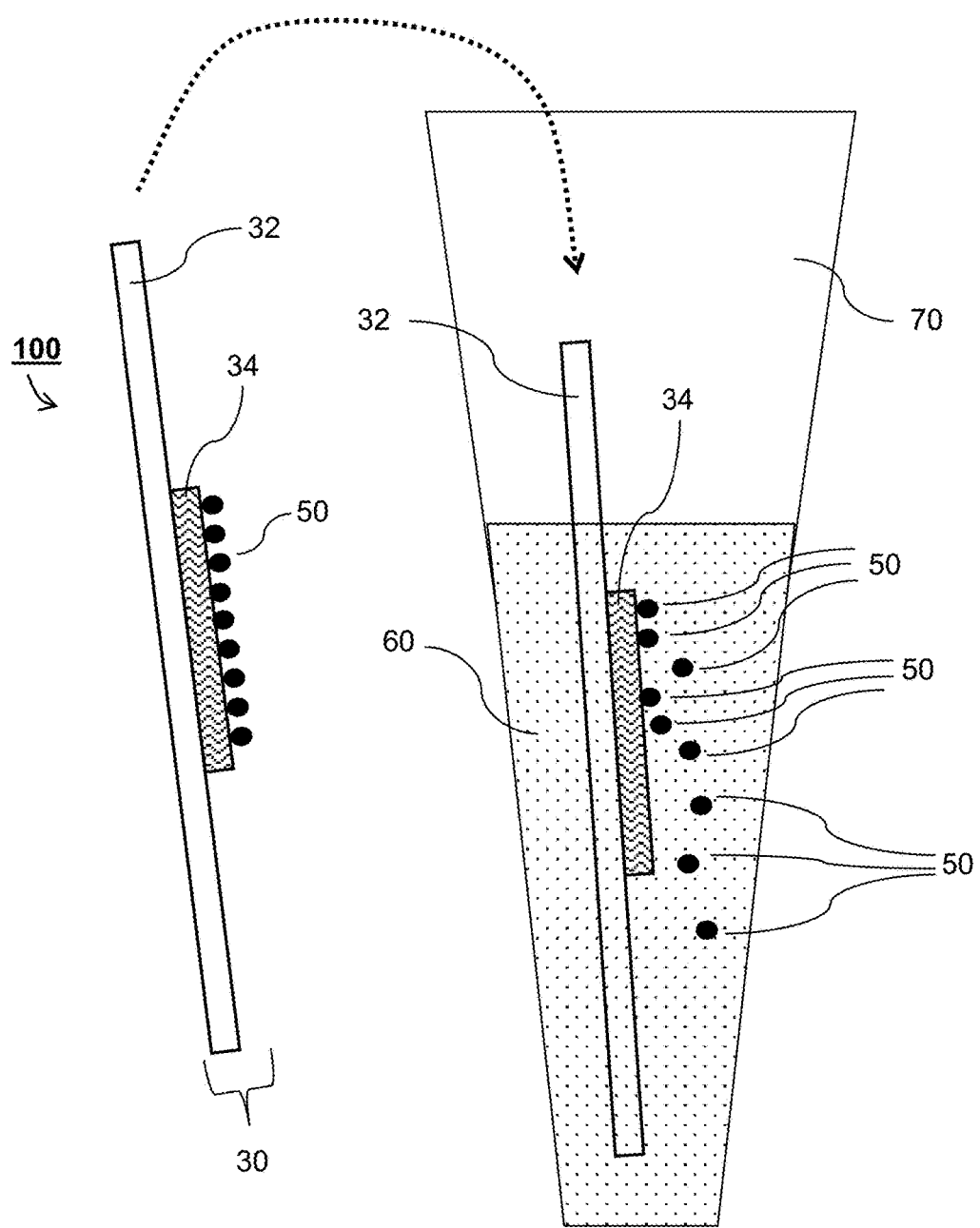
Figure 2E:
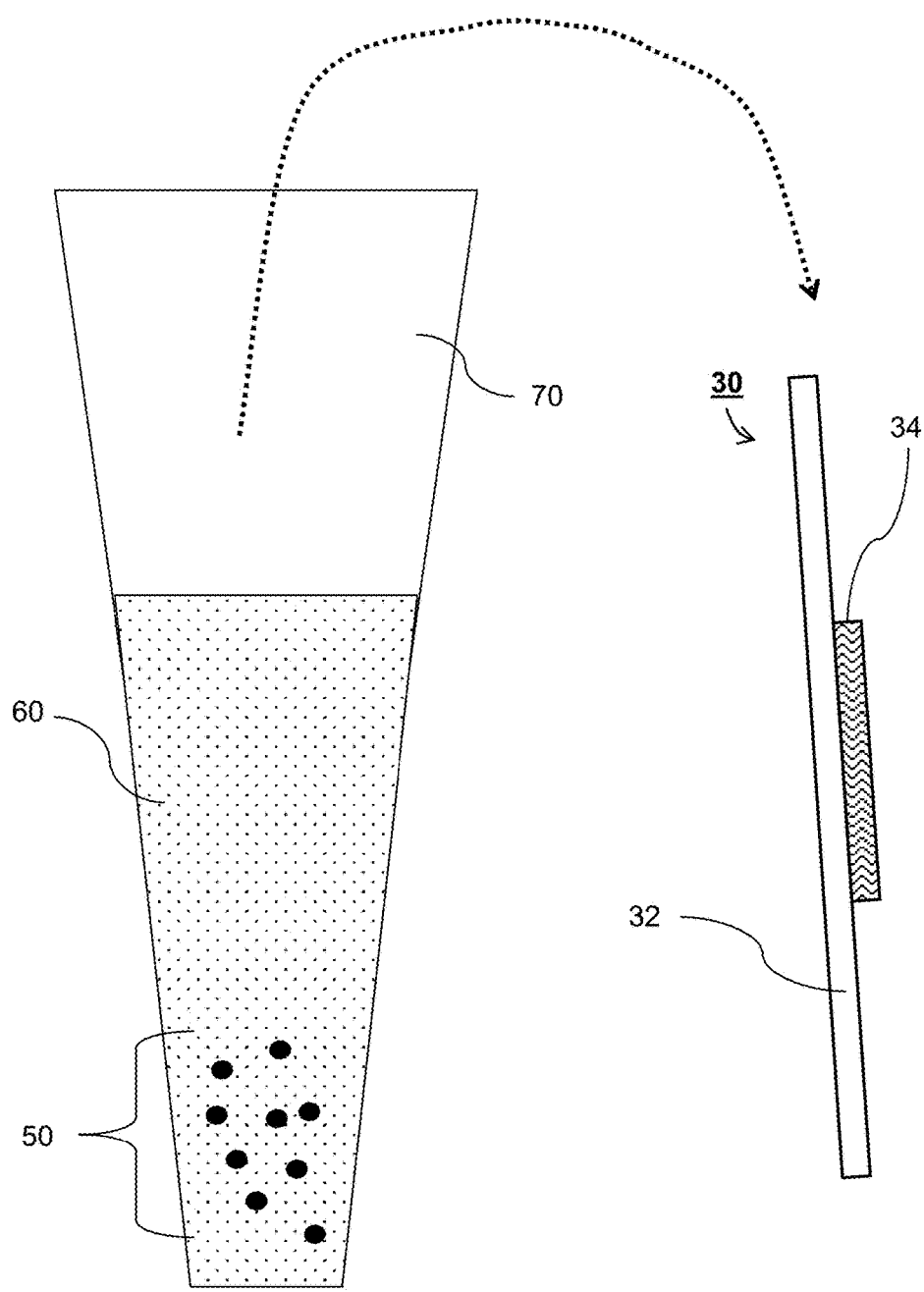

FIGS. 2D and 2E illustrate the elution of biomolecules from the peelable layer, and more specifically from the target component of the peelable layer. Because the target component remains bound to the substrate of the peelable layer during elution, it is possible to isolate and recover the biomolecules using elution techniques known by those of ordinary skill in the art.

As shown in FIG. 2D, after capturing biomolecules 50 on target component 34 of peelable layer 30, biomolecule elution strip 100 can be used to isolate and recover biomolecules 50 using elution techniques suitable for target component 34 and biomolecules 50. For example, biomolecule elution strip 100 can be subjected to elution buffer 60 contained in elution chamber 70 (e.g., a tube suitable for use in centrifuges and/or shakers), with elution buffer 60 being chosen for its effectiveness in providing a molecular reaction environment suitable to release biomolecules 50 from target component 34. The present invention contemplates the use of different types of buffers and concentrations to allow for graduated release, e.g., release of biomolecules having the least binding affinity using non-stringent buffers and the release of biomolecules having the most binding affinity using stringent buffers. For illustrative purposes, FIG. 2D shows biomolecules 50 at various stages of release from target component 34.

As shown in FIG. 2E, after an adequate amount of incubation/elution time, peelable layer 30 (i.e., substrate 32 with target component 34 bound thereto) can be removed from elution chamber 70, thereby isolating biomolecules 50 in elution buffer 60. According to elution/isolation techniques known in the art, biomolecules 50 can then be isolated for use in further applications such as, without limitation, screening and the like.

As shown in FIG. 2F, the present invention also contemplates the use of the devices and systems of the present invention to conduct affinity based screening, isolation, and recovery of multiple biomolecules using a single peelable layer having a single target component. However, the present invention also contemplates all configurations of peelable layer and target component.

FIG. 2F provides a schematic of views 1, 2, 3, and 4 that generally depict one embodiment for using the device of the present invention to isolate and recover biomolecules from a test sample.

In view 1 of FIG. 2F, test sample 80 is shown to include a plurality of different biomolecules, depicted as biomolecules 50a, 50b, 50c, and 50d. While test sample 80 is depicted as having the same number of each type of biomolecule, such depiction is only for illustration purposes, so that the present invention is not meant to be limited in this manner. Test sample 80 is then contacted to device 10. As set forth herein, applying the test sample to the device can be achieved by using an open delivery system and/or a closed delivery system. One of ordinary skill in the art, in view of the present disclosure, can determine the various buffers, solutions, parameters, and techniques suitable for applying the test sample to the device.

In view 2 of FIG. 2F, device 10 is shown to include support 20 with peelable layer 30 deposited thereon, and with peelable layer 30 including substrate 32 with target component 34 deposited thereon. View 2 of FIG. 2F also shows biomolecules 50a and 50c bound to target component 34, but biomolecules 50b and 50d not bound to target component 34, because biomolecules 50b and 50d do not have binding affinity to target component 34. This depiction is meant to illustrate that a single target component can capture more than one type of biomolecule (e.g., 50a and 50c), with each type of biomolecule having its own binding affinity to the target component. View 2 of FIG. 2F also shows a higher number of biomolecule 50a binding to target component 34 than biomolecule 50c. This depiction is meant to illustrate that one biomolecule (e.g., biomolecule 50a) can have a higher binding affinity to the target component than another biomolecule (e.g., biomolecule 50c), even though both biomolecules can bind with affinity to the same target component. This shows that a single target component can be used to capture, isolate, and recover more than one type of biomolecule contained in a single test sample. Therefore, as illustrated, the present invention can be used for affinity-based screening of a plurality of different biomolecules and other related applications.

In view 3 of FIG. 2F, peelable layer 30 is shown after being removed (e.g., peeled) from support 20, and after contacting target component 34 with test sample 80 containing biomolecules 50a, 50b, 50c, and 50d. As shown, once peelable layer 30 is removed, it yields biomolecule elution strip 100 having biomolecules (e.g., 50a and 50c) bound with affinity to target component 34. At this point, biomolecule elution strip 100 can be properly stored under conditions effective to maintain biomolecule elution strip 100 in such a way to allow for subsequent elution, recovery, and manipulation (e.g., screening) of the captured biomolecules. The present invention contemplates various modes of removing the peelable layer 30 from support 20, depending on the desired application. For example, removal (e.g., peeling) of peelable layer 30 from support 20 can be performed under dry or aqueous (wet) conditions. Aqueous conditions may be suitable if required to preserve the bioactivity/functionality of the recovered sample biomolecule (e.g., a cell).

In view 4 of FIG. 2F, peelable layer 30 is shown after elution of biomolecules 50a and 50c from target component 34. This view also depicts greater amounts of biomolecule 50a being eluted than biomolecule 50c. This depiction is meant to show how the present invention can be used for affinity based screening of multiple biomolecules to a single target component. The levels (e.g., amounts, concentrations) of each of the recovered types of biomolecules can be used to determine their affinities to the target component. Therefore, the present invention can be used for test samples that have one or more different types of biomolecules. Depending on the mixture of the sample, there could be more than one sample biomolecule binding to one peelable layer. For example, if biomolecule 50a binds very strongly to target component 34 and biomolecule 50c binds weakly to target component 34, then once peelable layer 30 is removed from support 20, it would be expected that more of biomolecule 50a would be recovered than biomolecule 50c.

As discussed herein, the present invention can be used for various applications, including, for example, for multiplexed affinity-based screening, e.g., whereby potential biomolecule candidates in a sample pool are screened against capturing targets (e.g., target biomolecules or target biomaterials) immobilized on an array surface. The present invention provides numerous potential combinations of how the device can be configured with one or more different target components, depending on the desired application.

FIGS. 3A-3D are schematic illustrations of one embodiment of the device of the present invention, which is provided to illustrate how multiple peelable layers are configured onto a single support.

Figure 3A:
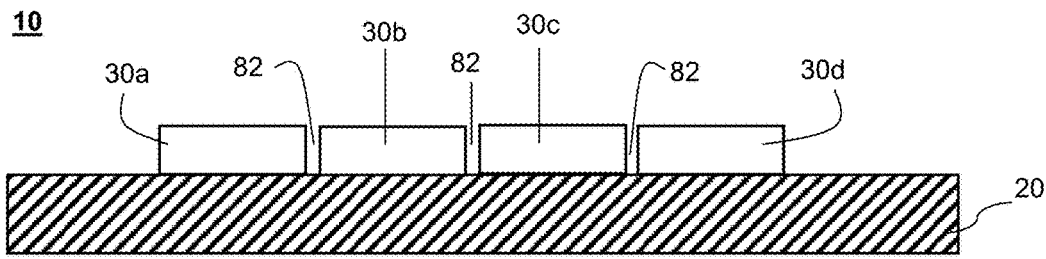
FIGS. 3A-3D are schematic drawings of various illustrative embodiments of the device of the present invention. These figures show multiple peelable layers (30a, 30b, 30c, and 30d) having their own substrates (32a, 32b, 32c, and 32d) and target components (34a, 34b, 34c, and 34d), with different biomolecules (50a, 50b, 50c, and 50d) having affinity to their respective target components.

FIG. 3A shows support 20 having four different peelable layers (30a, 30b, 30c, and 30d) removably deposited on support 20. As described in more detail herein, one method of configuring the device to include multiple peelable layers is to first deposit a single substrate layer onto support 20 and then to insert partitions 82 to yield multiple peelable layers. The partitions (e.g., boundaries) can be formed as described herein.

Figure 3B:
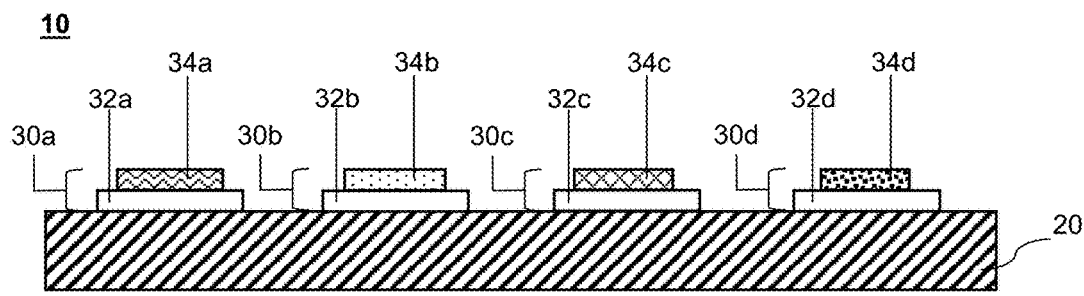

As shown in FIG. 3B, in one embodiment, device 10 can include multiple peelable layers, whereby each peelable layer (30a, 30b, 30c, and 30d) can include its own substrate (32a, 32b, 32c, and 32d) having its own target component (34a, 34b, 34c, and 34d) deposited thereon.

Figure 3C:
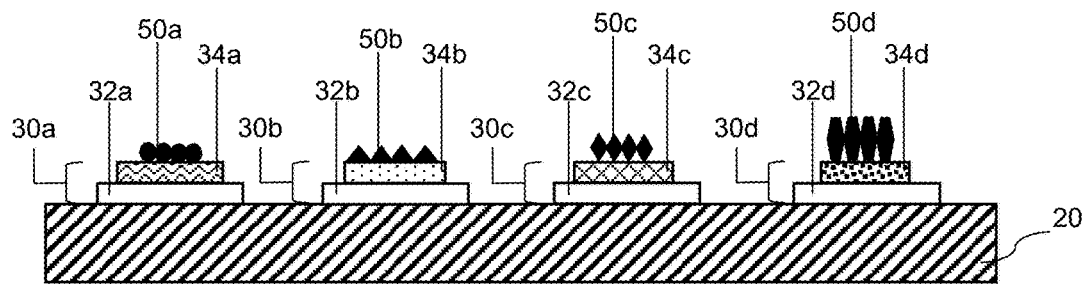

As shown in FIG. 3C, each target component (34a, 34b, 34c, and 34d) of each peelable layer (30a, 30b, 30c, and 30d) can be configured to be selective for a different biomolecule (50a, 50b, 50c, and 50d). Each peelable layer can be removed from the support independently from one another.

Figure 3D:
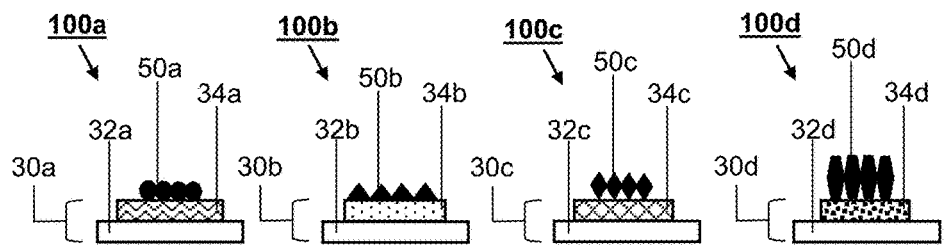

As shown in FIG. 3D, device 10 (FIGS. 3A and 3B) can be used to produce a plurality of biomolecule elution strips (100a, 100b, 100c, and 100d), with each strip having a different biomolecule (50a, 50b, 50c, and 50d) removably captured thereon. As discussed herein, each biomolecule elution strip can be used to recover their respective biomolecules, either immediately after capture or after storage of the biomolecule elution strip for subsequent recovery of the biomolecules.

EXAMPLES

The following examples are intended to illustrate particular embodiments of the present invention, but are by no means intended to limit the scope of the present invention.

Example 1

Multiplexing Aptamers Separation and Recovery with Parylene Peel-Strips

This example describes fabrication and a method of using an array of parylene-based "peel-able" strips (Peel-Strips) to screen and capture aptamers from a mixture onto specific proteins immobilized on the Peel-Strips, and subsequently isolate and recover each separated aptamer of interest by easily peeling off each strip. The Peel-Strips were also incorporated in a microfluidics format for low reagent volume consumption and to increase portability.

Model aptamers-proteins interactions were used to test the versatility of the platform for both nucleic acids and proteins. Specifically, VEGF, thrombin, and PDGF-BB were chosen as they play important roles in regulating endothelial cells: blood clotting, angiogenesis, permeability, and/or tumor progression [A9].

1.1—Fabrication of Parylene Peel-Strips 2 g of parylene C (diX-C, Uniglobe Kisco) was conformally coated onto diced pieces of square silicon substrate via chemical vapour deposition (CVD) using a Specialty Coating Systems Labcoter 2. This relatively thicker (~2.5 μm) layer of parylene C served as mechanical support to enable easy peeling and handling. 0.25 g of parylene A (diX-A, Uniglobe Kisco) was deposited on top of the parylene C layer using the same CVD process. This thin layer (250 nm) of parylene A conferred the substrate surface with amine groups suitable for covalent immobilization of proteins. Rectangular strips of polydimethylsiloxane (PDMS) were mechanically cut and placed on top of the parylene layers to serve as an etch mask and protect the underlying parylene from being etched. The parylene peel-strips were then defined by etching the area around the rectangular PDMS strips by oxygen plasma. The boundaries of the peel-strips can also be simply created by mechanically scoring with a razor blade, or more sophisticatedly with photolithography if strip widths as small as 10 s of micrometers are desired.

1.2—Covalent Immobilization of Proteins onto Parylene A

Figure 4A:
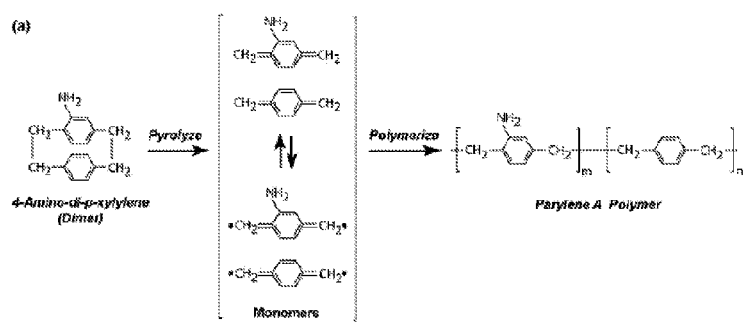
FIGS. 4A-4B are schematic drawings showing: (a) Parylene-A chemical structure and the CVD deposition process (FIG. 4A), and (b) covalent linkage of proteins to the parylene Peel-Strip surface (FIG. 4B).
Figure 4B:
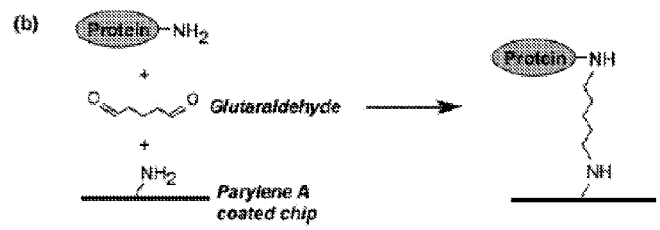
Figure 5A:
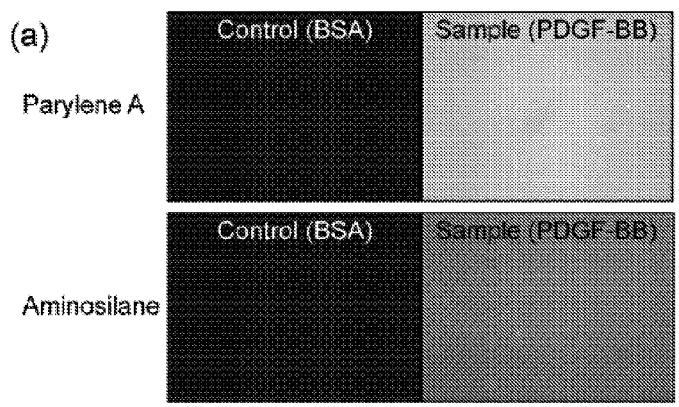
FIGS. 5A-5B provide results showing that a model protein (PDGF-BB) can be covalently immobilized onto the Peel-Strip surface, as shown by fluorescence immunostaining Aminosilane slide is used as a comparison of immobilization efficiency vs. parylene A. BSA protein is used as a control protein to show little non-specific binding.
Figure 5B:
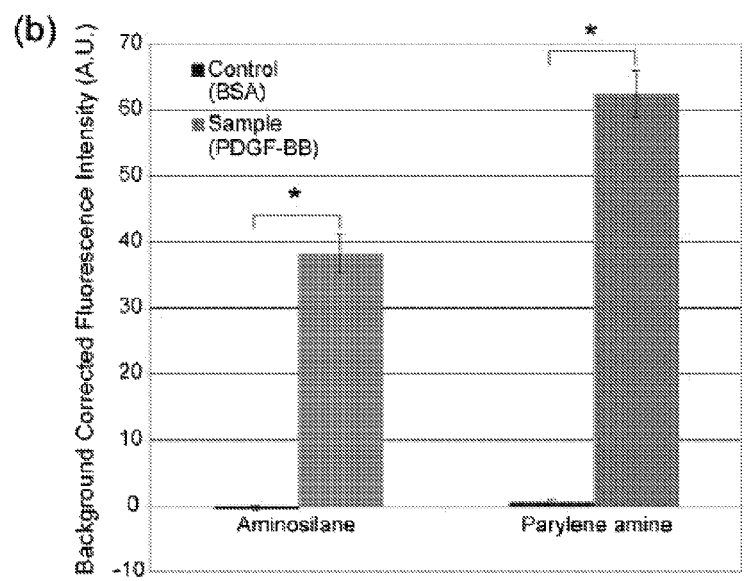
Figure 6A:
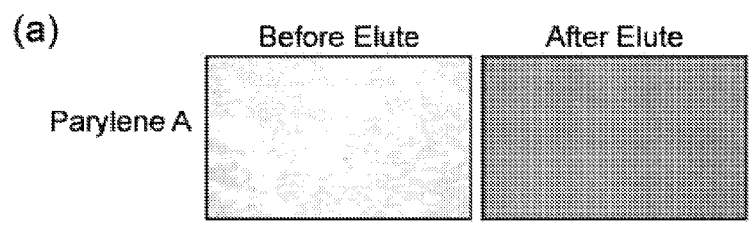
FIGS. 6A-6B show fluorescence measurements of the peel-strip surface before and after eluting off Alexa-594 aptamer bound to PDGF-BB. The captured aptamer can be eluted off and recovered.
Figure 6B:
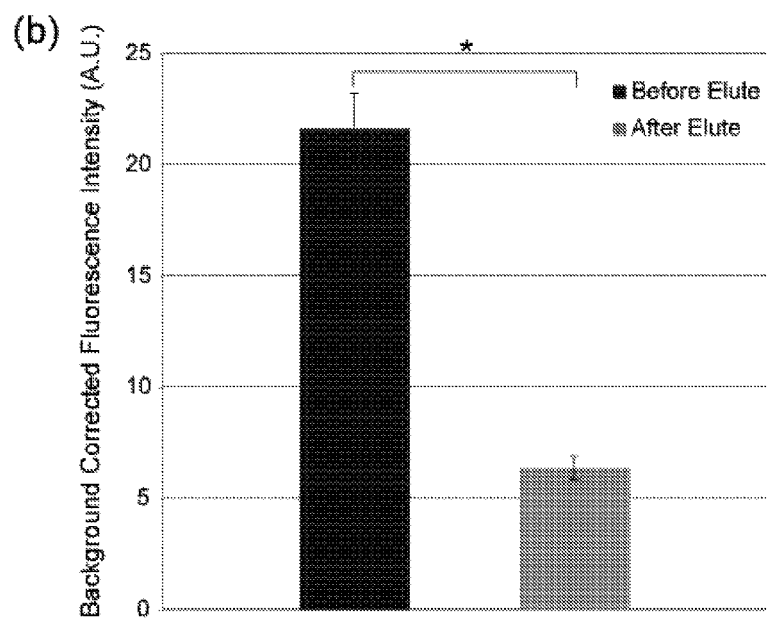

The parylene A surface was treated with 5% glutaraldehyde, a homobifunctional linker that would covalently cross-link amine groups on the parylene A surface and the proteins. The schematic in FIG. 4 shows a method for this surface chemistry. Proteins, namely platelet derived growth factor B-B dimer (PDGF-BB, Abcam), thrombin (Abcam) and vascular endothelial growth factor (VEGF, R&D Systems) were incubated onto the parylene A strips at a 1 μM concentration for 1 hour. The chips were blocked with 1% bovine serum albumin in phosphate buffered saline for 1 hour.

1.3—Aptamers Binding

For the no fluidic configuration, a drop of binding solution (10 mM Tris-HCl/MgCl$_2$) containing aptamers were incubated on the peel-strips surface.

1.4—Incorporation into Microfluidics

Figure 8E:
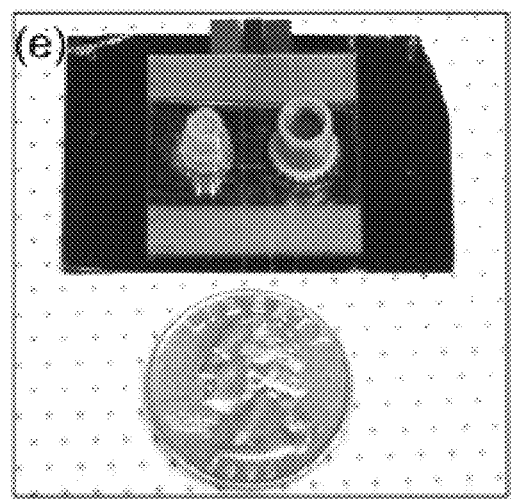

A silicone (PDMS) gasket containing a fluidic channel was placed on top of the parylene peel-strips array and sealed with a glass coverslip containing fluidic ports. A solution containing a mixture of aptamers in binding buffer were flowed into the microfluidic channel through the fluidic ports using a peristaltic pump (FIG. 8B). Binder clips were used to clamp and seal the whole microfluidic construction (FIG. 8E).

1.5—Aptamers Recovery

Figure 8F:
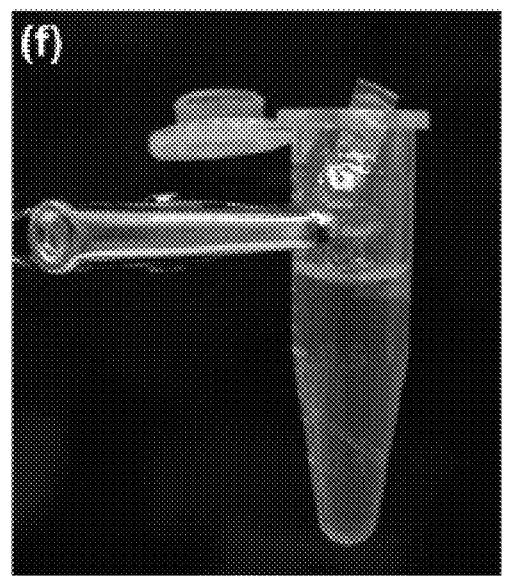

Each peel-strip containing the bound species of aptamer was mechanically peeled off using sterile tweezers (FIG. 8C) and placed inside a tube containing an eluting solution of 10 mM Tris-HCl/0.2% Tween-20 (FIGS. 8D-8F). After 10 minutes the tube was centrifuged and the eluting solution containing the aptamers were retrieved by a pipet.

1.6—Statistical Analysis

A Student's t-test was used to determine statistical significance, with p<0.01 being defined as significant. For the image analysis, at least n=3 images were averaged for each experimental condition. The bar graphs show the average values and the error bars indicate standard deviations.

1.7—Results and Discussion

As shown in this example, a simple chip was developed for the separation and recovery of aptamers from a mixture using affinity-based separation by proteins. This is not limited to screening and recovering aptamers-proteins, but could also extend to protein-protein, protein-cells interactions, nucleic acids hybridization etc. Further, this technology can be scaled up to produce smaller strips and smaller spots, e.g. 96-wells format. This can be automated using robotics. High-density Peel-Strips could then be peeled off to recover sample of interest. This can be extended to other fields such as the screening and selection of rare stem cells, induced pluripotent stem cells etc. Future use of the chip could also include drug Screening, whereby the chip is a simple affinity-based separation and recovery of aptamers as therapeutic molecules to target VEGF, PDGF-BB and thrombin.

Example 2

Multiplexed Aptamers Selection and Recovery with Parylene Peel-Strips

This work reports on the fabrication and use of the novel parylene-based "peelable" strips (Peel-Strips) array surface that combines both affinity-based screening and recovery of aptamers from a sample pool. Parylene-A layer was used to confer amine groups to the Peel-Strips for the covalent immobilization of a different protein on each strip. The Peel-Strips array patterned with proteins were then incorporated into a microfluidic format and exposed to a sample mixture containing aptamers for affinity-based screening. Microfluidics enable low reagent volume consumption through the miniaturization. Afterwards, each individual Peel-Strip could be simply peeled off to recover the aptamers that bound to the specific protein. As an initial proof of principle, aptamers known to bind to proteins implicated in disease (thrombin, VEGF, PDGF-BB) were tested for affinity binding and recovery. Aptamers recovery was quantified via fluorospectrometry and rolling circle amplification. Aptamer concentrations down to 1.6 nM could be recovered and detected, depending on the aptamer affinity for the protein of interest.

2.1—Fabrication of Peel-Strips 2.5 microns of parylene-C (diX-C, Uniglobe Kisco) was conformally coated onto 22 mm×22 mm thermally oxidized silicon chips via CVD using a Specialty Coating Systems Labcoter 2. This layer of parylene-C served as mechanical support to enable easy peeling and handling. 250 nm of parylene-A (diX-A, Uniglobe Kisco) was deposited on top of the parylene-C layer using the same CVD process, to confer surface amine groups suitable for protein immobilization. The boundaries of the Peel-Strips were created by mechanically scoring with a razor blade to create 3 mm wide rectangular strips. For future work in miniaturizing the Peel-Strips further, Peel-Strips with micrometer lengths and widths can be easily defined with photolithography and oxygen plasma etching as previously described for microfabrication of parylene stencils [11].

2.2—Covalent Immobilization of Proteins onto Peel-Strips

Figure 7:
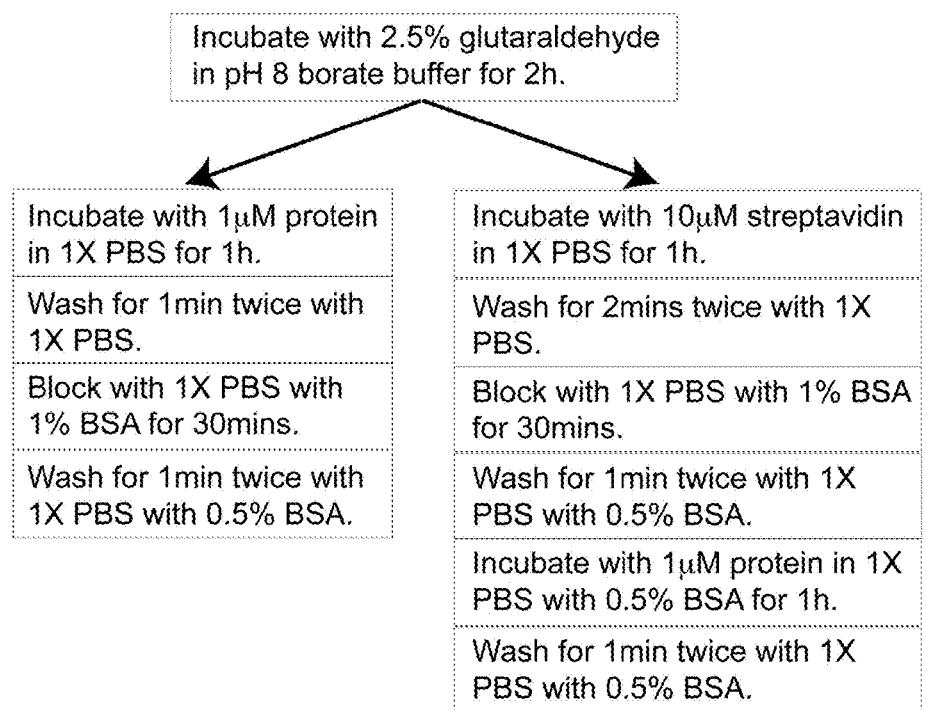
FIG. 7 is a diagram showing the process flow of protein immobilization onto Peel-Strips surface.

The top surface of the Peel-Strips (parylene-A layer) was treated with 500 µL of 2.5% glutaraldehyde, a homobifunctional linker that would covalently cross-link amine groups on the Peel-Strip surface and the proteins [15]. The schematic in FIG. 4 outlines the surface chemistry, while FIG. 7 shows the process flow. To attach a biotinylated protein to the surface, the process was modified to first immobilize streptavidin with the surface amine groups, followed by incubation with the protein of interest (FIG. 7). The proteins used in this study are listed in Table 1. All the incubation reactions were performed on the chips inside a humidified dish to reduce evaporation and prevent the solution droplets from drying out.

2.3—Fluorescent Immunostaining to Detect Protein Covalently Immobilized on Parylene-A Proteins were immobilized on test chips coated with 250 nm of parylene-A as described. Fluorescent was performed immunostaining using a primary antibody against the protein and a corresponding fluorophore conjugated secondary antibody, to confirm the presence of the protein on the surface. Chips immobilized with BSA served as negative controls for the fluorescent immunostaining. The primary antibodies were purchased from the same sources as the protein antigens in Table 1. AlexaFluor labeled secondary antibodies were obtained from Invitrogen. The primary antibodies were incubated on the chips at 50 µg/mL diluted in 1×PBS with 0.5% BSA for 1 h, and then washed twice for 2 mins with 1×PBS with 0.5% BSA. Afterwards, the secondary antibodies were diluted 1:100 in 1×PBS with 0.5% BSA for 1 h, and also washed similarly as before. Chips were imaged using fluorescence microscopy (Olympus AX70) using filter cubes designed for the specific fluorophores.

TABLE 1

Proteins used in this study

| Protein | MW (kDa) | Source |
| --- | --- | --- |
| Human TNF-α | 17.5 | R&D Systems |
| Human VEGF$_{165}$ | 20 | R&D Systems |

TABLE 1-continued

Proteins used in this study

| Protein | MW (kDa) | Source |
|---|---|---|
| Human PDGF-BB | 24.3 | Abcam |
| Human PSA | 30 | Biodesign International |
| Human α-Thrombin | 37 | Haematologic Technologies |
| Human biotinylated α-Thrombin | 37 | Haematologic Technologies |

2.4—Fluorescence Assay to Test for Bioactivity of Covalently Immobilized Thrombin Since α-thrombin is a serine protease, it was convenient to also test the bioactivity of the covalently immobilized enzyme. SN-59, a fluorogenic substrate for thrombin, was purchased from Haematologic Technologies and used to probe the bioactivity of thrombin. 10 μM of BSA and thrombin were immobilized on parylene-A coated chips and three 2 μL drops of 100 μM SN-59 were incubated on the chips. The BSA chip served as a negative control for this assay. The fluorescence of the drop on the chip surface was imaged using fluorescence microscopy after 60 mins. As a comparison, the reaction of thrombin with SN-59 in free solution was also tested. SN-59 and thrombin were mixed in a 50 μL volume inside a microcentrifuge tube at 100 μM and 1 μM final concentrations. The control tube contained a SN-59 and BSA mixture. Three 24 drops of each mixture were removed at 0, 20, 30, 45, and 60 mins, and imaged using fluorescence microscopy on a glass coverslip. The fluorescence of the three drops on each chip was averaged for each time point.

2.5—Fluorescence Microscopy Image Analysis

At least three images were collected at random positions on each chip for the analyses, both from the center of the chip where the protein was incubated and the peripheral region of the chip where no protein was incubated (background). Fluorescence intensity per pixel was recorded for each image using the histogram function in ImageJ software (National Institutes of Health). For background correction on each chip, the average fluorescence signal from background was subtracted from the average fluorescence signal from the center region.

2.6—Incorporation of Peel-Strips with Microfluidics Assembly

Table 2 lists the flow conditions used for the microfluidic experiments. 10 μL of each protein was spotted and immobilized on each Peel-Strip as described. A 1 mm thick silicone gasket (Grace Biolabs) defined with a 4 mm wide×20 mm long fluidic channel was placed on the parylene Peel-Strips and sealed at the top with a 1 mm thick glass coverslip containing two fluidic ports as shown in FIGS. 8A, 8B, and 8E. The NanoPort (Idex) at the outlet reservoir enabled mating with tubing connected to a peristaltic pump (Idex) that controlled the flow rate by withdrawing fluid. Two binder clips were used to clamp and seal the whole microfluidic assembly. Binding buffer (20 mM Tris-HCl, 140 mM NaCl, 5 mM KCl, 1 mM $MgCl_2$, 1 mM $CaCl_2$) was utilized for all the microfluidic aptamer experiments. The coverslip and gasket can be reversibly separated from the chip to facilitate peeling of the Peel-Strips. Table 3 summarizes the samples flowed in various microfluidic experiments.

TABLE 2

Microfluidic chip flow conditions

| Step | Reagent | Flow Rate (μL/min) | Time (min) | Total Volume (μL) |
|---|---|---|---|---|
| Filling fluidic channel | Binding buffer | 20 | 1 | 20 |
| Introduce aptamers | Sample (see FIG. 9) | 20 | 5 | 100 |
| Wash | Binding buffer with 0.5% BSA | 40 | 2.5 | 100 |

TABLE 3

Samples introduced in various microfluidic experiments

| Experiment | Sample |
|---|---|
| Binding of known fluorescent aptamers | Fluorescent aptamers mixed in binding buffer to a final 5 μM concentration each. |
| Binding of RCA aptamer-primers | Thrombin and PDGF-BB aptamer-primers mixed in binding buffers to final concentrations of 5 μM, 1 μM, 200 nM, 40 nM, 8 nM, 1.6 nM each. |

2.7—Individual Recovery of Bound Fluorescent Aptamers by Peel-Strips

All DNA sequences were purchased and purified by Integrated DNA Technologies. Known aptamer sequences for thrombin [17], PDGF-BB [18], and VEGF [19] were modified to contain the fluorophore AlexaFluor 488, 594, and 647 respectively (Table 4). Each Peel-Strip containing the bound aptamers was mechanically peeled off using sterile tweezers (FIG. 8C) and placed inside a microcentrifuge tube. Milty Zerostat3 was used to neutralize static charges on the strips. 20 mM sodium hydroxide (FIGS. 8D-8F) was added to elute off the aptamers. After 1 min, the sodium hydroxide solution was retrieved by a pipette into a clean tube and neutralized with a 1M hydrochloric acid. Each strip was washed again with 104, deionized water, which was then collected and pooled with the previous eluent. Relative amounts of fluorescent aptamers eluted from each strip were detected using a Nanodrop ND3300 fluorospectrometer.

2.8—Rolling Circle Amplification of Recovered Aptamers

Figure 10:
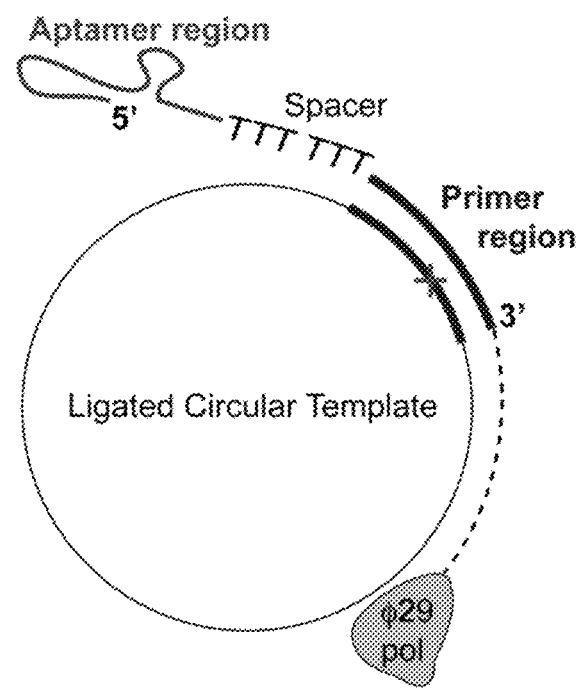
FIG. 10 is a schematic of an RCA detection scheme. Each aptamer was designed to carry a primer region that was complementary to a specific ligated circular template. Note that the sequences of the PDGF-BB and thrombin ligated circular templates are different and unique as shown in FIG. 9. Upon successful hybridization of the primer region to the correct template, the ϕ29 polymerase then continuously amplify and displace the growing ssDNA strand from the circle template. Hence, a large MW ssDNA product is created if and only if the aptamer bearing the correct primer region is present.

Rolling circle amplification (RCA) was exploited as a more sensitive detection method to analyze the recovered aptamers, since some of the aptamers used (e.g. thrombin-aptamer with 15 bases) were too short to be used as a template for PCR. The known aptamers for thrombin and PDGF-BB tested in Section 2.7 were each modified to contain a unique primer region (aptamer-primer, sequences shown in FIG. 9). In the presence of the aptamer-primer with sequence complementary to the circular template, the highly processive isothermal φ29 polymerase linearly amplifies and also displaces the growing ssDNA strand continuously to create a large MW RCA product (FIG. 10).

Phosphorylated ssDNA template with the complementary sequence to the each aptamer-primer (FIG. 9) was ligated using CircLigase I enzyme from Epicentre Biotechnologies (Table 4) to create the circular templates. Unligated ssDNA templates were removed via ExoI/III digestion. To verify successful ligation, 2 µL of the ligase reaction were loaded and electrophoresed in a 10% TBE urea denaturing polyamcrylamide gel (Novex, 180V, 40 mins), together with the negative controls of unligated ssDNA template and unligated ssDNA template with ExoI/III treatment.

RCA was performed under the conditions in Table 5. After polymerase inactivation, 5 µL of each RCA reaction were loaded into a 1% agarose gel and electrophoresed to visualize the large MW RCA products. Table 6 shows the design of experiment for microfluidic selection and recovery of the aptamer-primers by Peel-Strips functionalized with thrombin, PDGF-BB, and VEGF. Aptamer-primers eluted from each strip were probed with thrombin and PDGF-BB circular templates to confirm the correct capture of the aptamer-primer by the proteins and nonspecific binding if any. Mixtures of aptamer-primers with 5-fold concentration dilutions were used in the microfluidic experiments to determine the limit of detection of RCA.

TABLE 4

Reaction for ligating phosphorylated ssDNA

| Components | Stock | Final Concentration | Volume (µL) |
|---|---|---|---|
| Phosphorylated ssDNA template | 10 µM | 0.5 µM | 2 |
| 10X CircLigase reaction buffer | 10X | 1X | 4 |
| ATP | 1 mM | 50 µM | 2 |
| Manganese chloride | 50 mM | 2.5 mM | 2 |
| CircLigase I* | 100 U/µL | 5 U/µL | 4 |
| Water | | | 26 |
| | | Total volume | 40 |

*Heat mixture at 95° C. for 5 mins and snap cool on ice before adding CircLigase I.
Incubate at 60° C. for 2 h.
Inactivate ligase at 80° C. for 10 mins and snap cool on ice.
Add 1 µL each of ExoI (stock 20 U/µL) and ExoIII (stock 200 U/µL).
Incubate at 37° C. for 1 h.
Inactivate exonucleases at 80° C. for 15 mins.

TABLE 5

RCA reaction conditions

| Components | Stock | Final Concentration | Volume (µL) |
|---|---|---|---|
| Circular template | Ligase reaction | N/A | 2 |
| Aptamer-primer | Eluent from Peel-Strip | N/A | 4 |
| 10× RepliPHI buffer | 10X | 1X | 1 |
| dNTP | 25 mM each | 2.5 mM | 1 |
| DTT | 100 mM | 5 mM | 0.5 |
| φ29 polymerase | 100 U/uL | 5 U/uL | 0.5 |
| Water | | | 1 |
| | | Total volume | 10 |

Incubate at 30° C. for 3 h. Inactivate polymerase at 65° C. for 10 mins.

TABLE 6

RCA design of experiment for testing Peel-Strips eluent

| Eluent from Peel-Strip of: | PDGF-BB | PDGF-BB | Thrombin | Thrombin | VEGF | VEGF |
|---|---|---|---|---|---|---|
| Perform RCA | PDGF-BB | Thrombin ligated | PDGF-BB | Thrombin ligated | PDGF-BB | Thrombin ligated |

TABLE 6-continued

RCA design of experiment for testing Peel-Strips eluent

| with circular Template: | ligated circle | circle | ligated circle | circle | ligated circle | circle |
|---|---|---|---|---|---|---|

2.9—Statistical Analyses

Student's t-test was used to determine statistical significance (p<0.01). At least n=3 replicate chips were used for each experiment. Furthermore, three images at random positions were taken on each chip. These measurements were then averaged. The bar graphs show the average values and the error bars show standard deviations.

Figure 11:
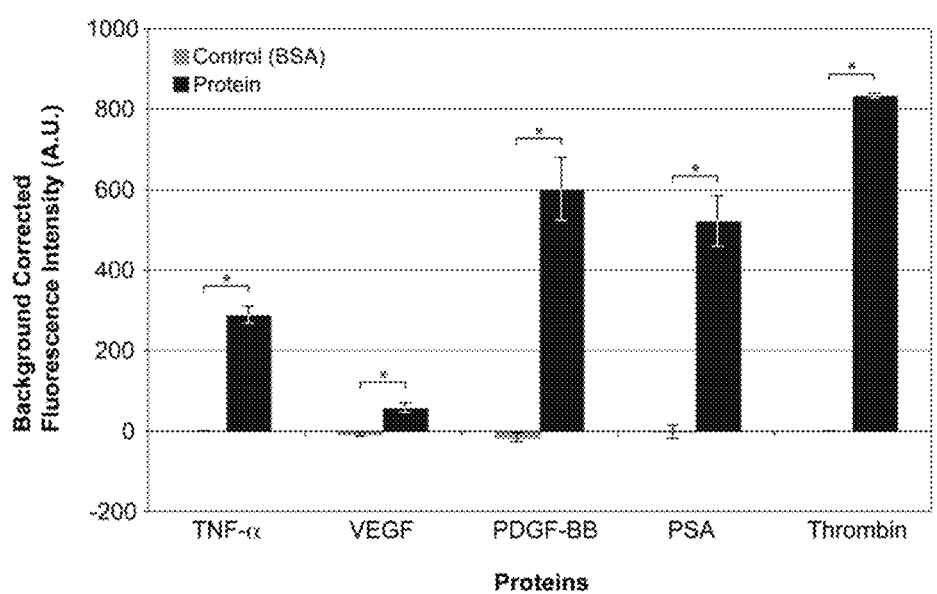
FIG. 11 is a graph showing fluorescent immunostaining of covalently immobilized proteins on parylene-A coated chips. Chips functionalized with BSA served as a control for each protein-antibody pair tested. All proteins tested are present on the parylene-A surface.

Results and Discussion 2.10—Presence of Covalently Immobilized Proteins on Peel-Strips FIG. 11 shows the fluorescent immunostaining results of various proteins immobilized on the Peel-Strips. Compared to the control (BSA) surface, the chips that have been incubated with proteins show a statistically significant increase in fluorescence due to the antibodies detecting the proteins present on the surface (p<0.01). These results indicate that proteins of a range of molecular weights can be immobilized on the parylene-A surface. These findings are consistent with another report that showed antibody binding to proteins covalently linked to parylene-A coated polystyrene microplates [15].

Figure 12:
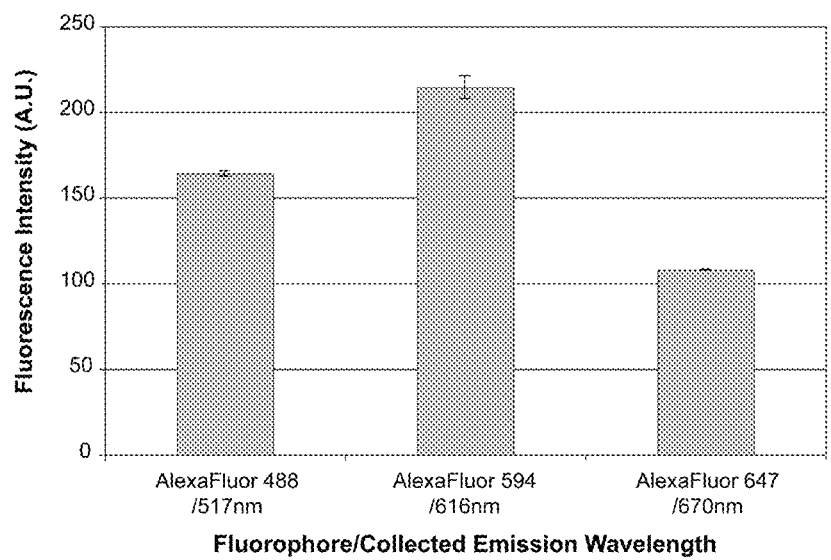
FIG. 12 is a graph showing autofluorescence of parylene-A corresponding to the emission wavelengths for different fluorophores.

However, the fluorescent immunostaining results can only be qualitative due to differences in the background fluorescence values at various excitation and emissions wavelengths. This is due to the background autofluorescence of parylene-A, which is shown in FIG. 12 collected at the emission wavelengths corresponding to different AlexaFluor fluorophores. The chips were excited at the optimum peak excitation wavelengths of the fluorophores. Parylene-A showed the highest autofluorescence at the 616 nm emission wavelength and the least autofluorescence at the 670 nm. Parylenes also have extraordinarily large autofluorescence at UV wavelengths and are rapidly bleached upon excitation (data not shown). To minimize interference from background autofluorescence, it is recommended to conduct fluorescence studies that involve parylene as the substrate at the red emission wavelengths. For this qualitative study simply to detect the presence or absence of proteins from the parylene-A surface, the autofluorescence of parylene did not pose a problem since the signals from the antibodies were much higher than the background autofluorescence.

2.11—Bioactivity of Immobilized Thrombin on Parylene-A

Thrombin is a serine protease that can recognize and cleave a range of peptide sequences, amongst which is the valine-proline-arginine sequence. SN-59 is a 6-amino-1-naphthalenesulfonamide based fluorogenic substrate for thrombin that contains the valine-proline-arginine sequence. Once cleaved from this peptide moiety, SN-59 exhibits a 1,000-fold increase in fluorescence intensity.

Figure 13A:
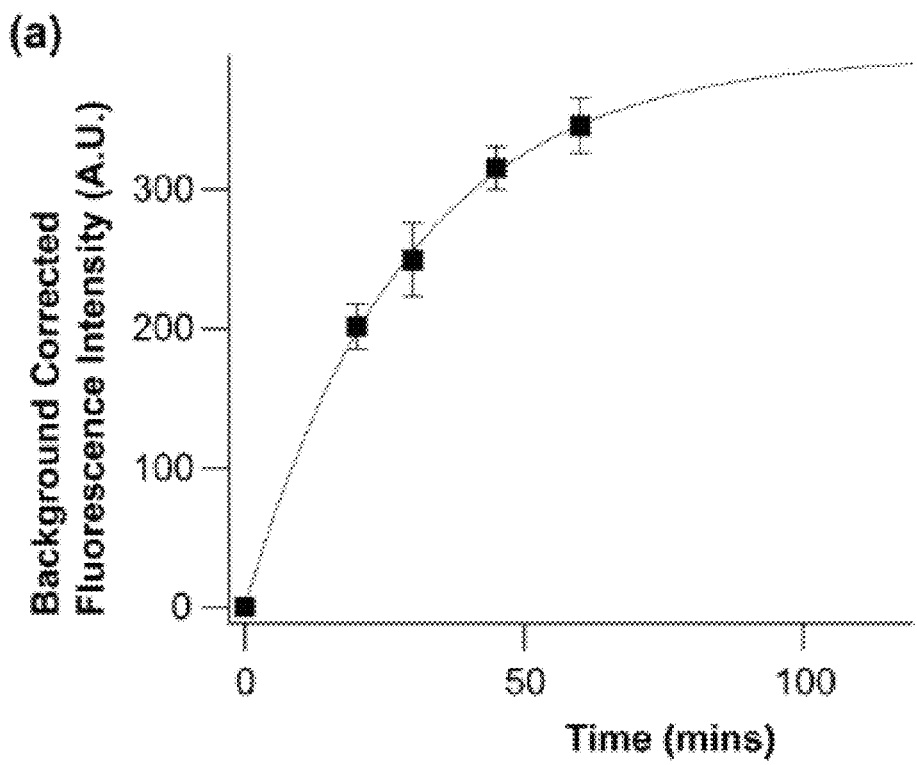
FIGS. 13A-13B are graphs showing fluorescence assay of thrombin cleaving the fluorogenic substrate SN-59 in (a) free solution at 10 μM thrombin concentration (FIG. 13A), and (b) immobilized thrombin incubated at 1 μM concentration (FIG. 13B).
Figure 13B:
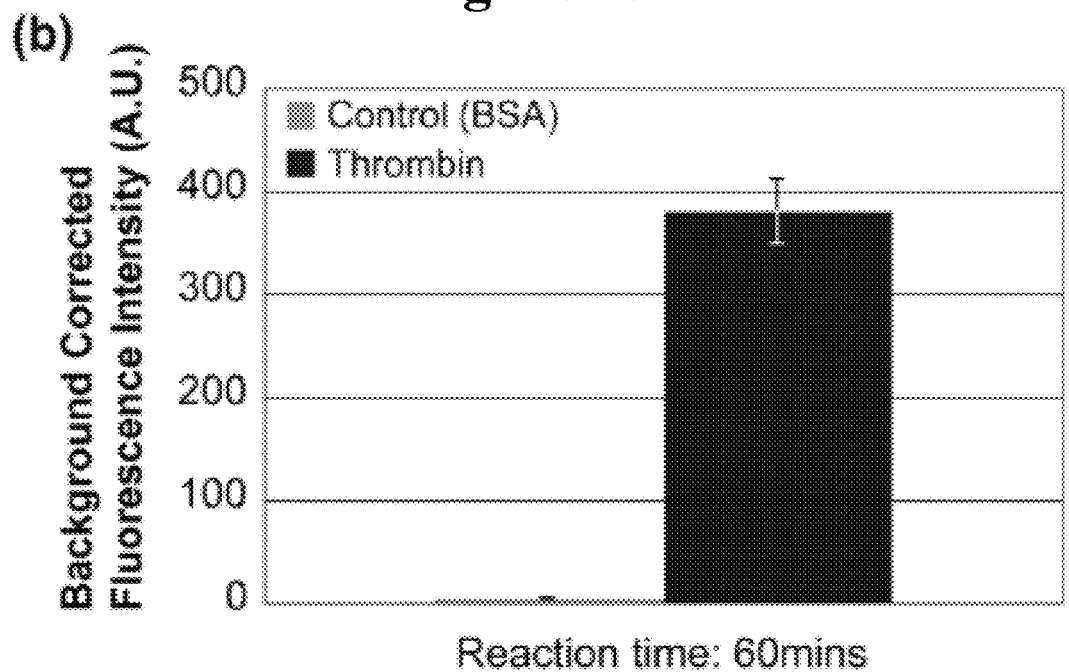

FIG. 13A shows the curve of fluorescence increase with time as more SN-59 was cleaved by thrombin in free solution. FIG. 13B shows a 300-fold increase in fluorescence of the chip immobilized with 10 μM thrombin compared to the control chip immobilized with BSA, comparable to the fluorescence of 1 μM thrombin incubated with the same SN-59 concentration in free solution.

While this one assay is not an exhaustive conclusion that thrombin bioactivity is wholly maintained, the results do indicate that immobilized thrombin retains some bioactivity, in this case for recognizing and cleaving the valine-proline-arginine peptide sequence. This result here is important to show that thrombin retains some bioactivity. Most studies thus far only test for the presence of immobilized proteins via antibody binding, but not the functional bioactivity of an immobilized protein on parylene-A surface [15, 20], except in one study by Lahann et al. whereby r-hirudin protein was immobilized in metallic implant devices to resist blood clotting in vivo [13].

Figure 14:
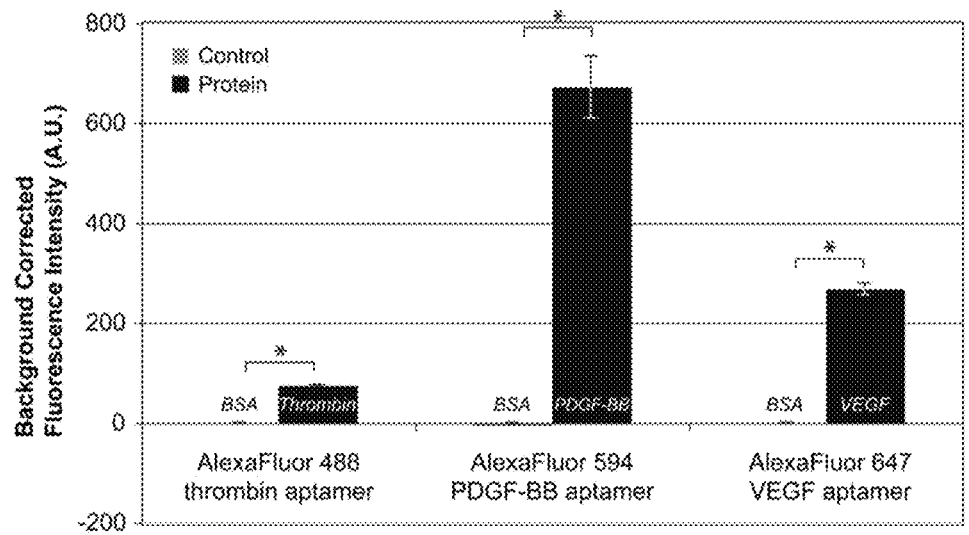
FIG. 14 is a graph showing fluorescence intensity showing aptamers binding to the correct proteins tested (thrombin, PDGF-BB, and VEGF, *p<0.01). Aptamers showed little to no binding to the BSA control chips. The thrombin protein (biotin-thrombin) was immobilized on the Peel-Strip via indirect streptavidin linkage, and the corresponding control chip was functionalized with biotin-BSA.

2.12—Binding of Fluorescent Aptamers to Proteins Immobilized on Peel-Strips in Microfluidics Fluorescently labeled known aptamers for thrombin, PDGF-BB, and VEGF (FIG. 9) were first individually tested for binding to proteins immobilized on parylene-A coated chips, following similar process steps as the fluorescent immunostaining studies but only using aptamer instead of antibodies. FIG. 14 shows the successful binding of the fluorescent aptamers to their corresponding proteins ($p<0.01$). Control chips with BSA showed little to no fluorescent signal (no binding). Even though immobilized thrombin was present on the chips as verified by fluorescent immunostaining in Section 2.10 and its bioactivity was retained in Section 2.11, however the 15-mer AlexaFluor 488 thrombin-aptamer did not bind to thrombin (data not shown). The thrombin-aptamer could only bind to biotinylated thrombin that was indirectly immobilized via streptavidin method described in FIG. 7. The thrombin in FIG. 14 was biotinylated and immobilized via streptavidin, and its corresponding control chip was functionalized with biotin-BSA.

Figure 15:
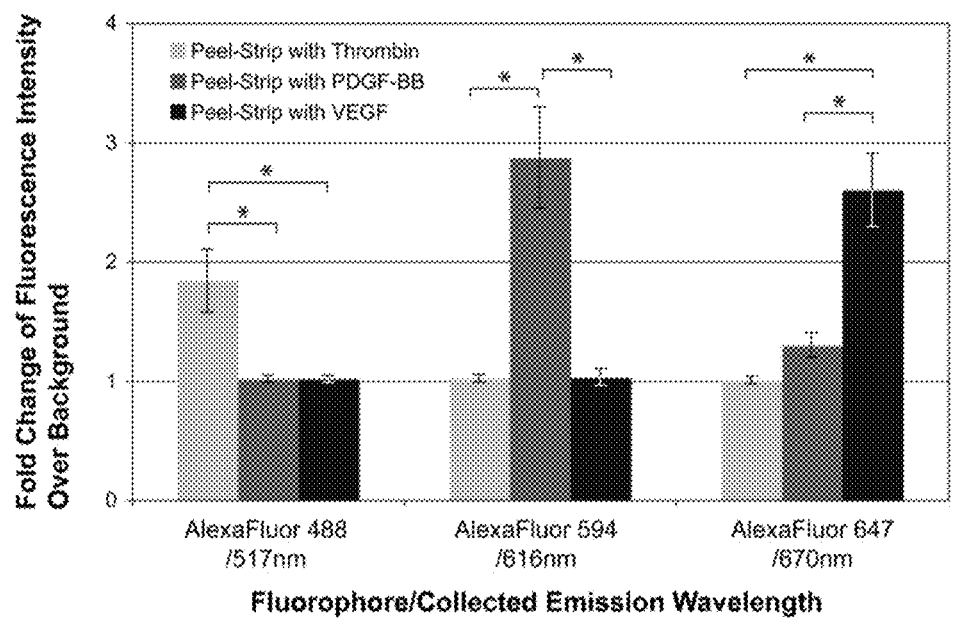
FIG. 15 is a graph showing fluorescence microscopy of Peel-Strips showing aptamers binding to the correct proteins (*p<0.01). Fluorescence intensities are normalized over the background as fold-changes to account for differences in parylene-A autofluorescence over the various emission wavelengths.

The fluorescent aptamers were then mixed in a 100 μL volume to 5 μM final concentrations (FIG. 9) and flowed through the microfluidic Peel-Strips device. Three Peel-Strips are present in each microfluidic device and each strip was spotted and immobilized with a different protein. After washing, the glass coverslip and silicone gasket were removed from the chip. Each individual Peel-Strip was imaged using fluorescence microscopy before peeling off (FIG. 15) to check for successful binding of the aptamer to the correct protein and also to test for non-specific binding. The results in FIG. 15 showed specific and high affinity binding of the aptamers for their corresponding proteins. The AlexaFluor 647 VEGF-aptamer showed some non-specific binding for PDGF-BB protein on the Peel-Strip. Thrombin aptamer preferentially bound to the thrombin Peel-Strip to give a ~1.8 fold increase in fluorescence signal over the other strips, while PDGF-BB and VEGF aptamers gave a ~2.9 fold and ~2.5-fold increase respectively. Presumably, these differences in fold-increase of fluorescence are due to the different affinity of aptamers binding to the proteins, but could also be convolved with parylene-A autofluorescence. Hence, the captured fluorescent aptamers on each strip was eluted with sodium hydroxide and measured using fluorospectrometry to mitigate the issue of parylene autofluorescence.

Figure 16:
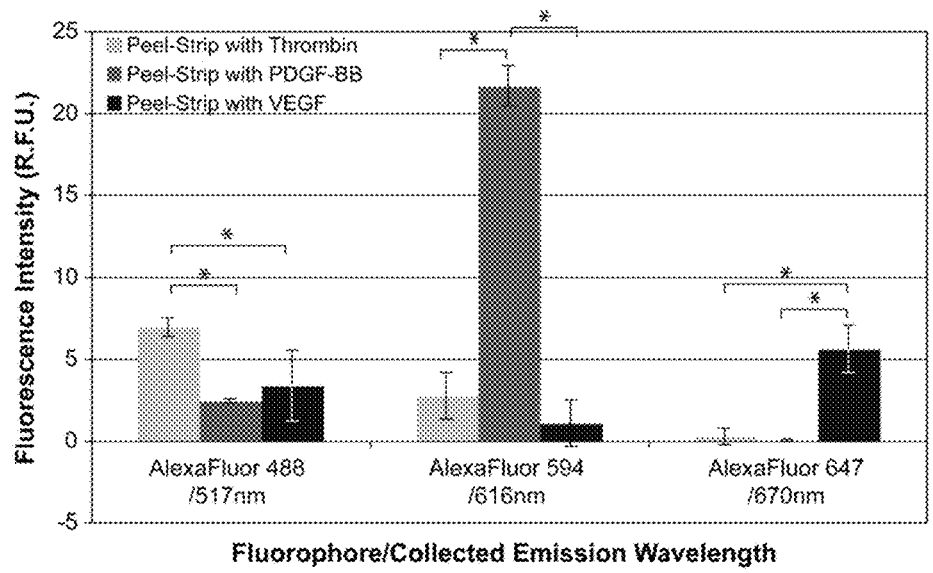
FIG. 16 is a graph showing fluorospectrometer measurements of aptamers eluted from different Peel-Strips confirming again that the aptamers bound specifically and with high affinity to the correct proteins compared to other nonspecific proteins (*p<0.01).

Fluorescence measurements of the eluted aptamers from each Peel-Strip by the fluorospectrometer confirmed that the aptamers bound specifically and with high affinity to their correct proteins, as shown in FIG. 16. However differences in the amount of nonspecific binding (albeit low) to the irrelevant proteins could be observed. While the aptamers still showed high signal binding to the correct proteins, the increase in fluorescence intensity over the irrelevant proteins are different from FIG. 15. The results in FIG. 16 should be more accurate in reflecting the affinity binding of aptamers to the proteins, since the problem of parylene autofluorescence is eliminated.

However, even though a relatively high concentration of fluorescent aptamers was used (5 μM each), unfortunately the fluorescence R.F.U. measured was already at the limit of detection of the fluorospectrometer. A more sensitive method for detecting the eluted aptamers is needed, such as RCA that is utilized in Section 2.13.

2.13—RCA of Aptamers Recovered by Microfluidic Peel-Strips

RCA was exploited as a potentially more sensitive detection method to analyze the recovered aptamers, since the limit of detection of fluorometry was reached in Section 2.12 and PCR-based methods are inapplicable due to the short aptamer length (the 15 bases long thrombin-aptamer is smaller than a PCR primer).

Figure 17:
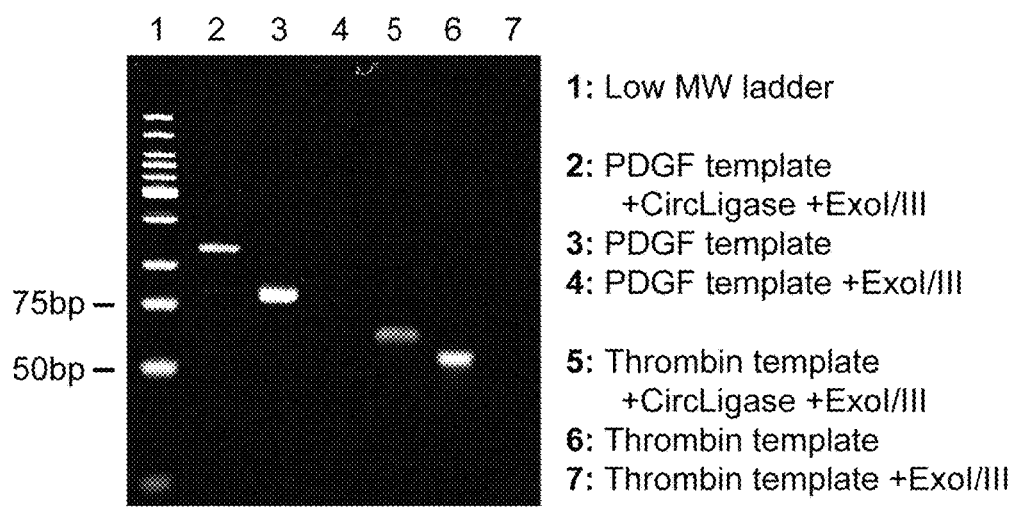
FIG. 17 is a diagram showing a 10% TBE urea denaturing polyacrylamide gel of ligated circle products. Circularized ssDNA (lanes 2, 5) migrates slower than linear ssDNA (lanes 3, 6). Additionally, circularized ssDNA is not digested by ExoI and III (lanes 2, 5), while linear ssDNA is digested by ExoI and III (absence of bands in lanes 4, 7). The PDGF-BB template (80 bases) has a different sequence from the thrombin template (53 bases).

The denaturing polyacrylamide gel in FIG. 17 shows that ligated circles were successfully ligated from 5'phosphorylated ssDNA templates (PDGF-BB template and thrombin template, FIG. 9). The electrophoretic mobility of circular ssDNA is slower than that of linear ssDNA, which can be seen from the upwards shift in the bands in lanes 2 and 5 (ligated circles) compared to the bands in lanes 3 and 6 (linear ssDNA). Another confirmation is the presence of the bands in lanes 2 and 5 after ExoI/III digestion, since circular DNA is not digested. On the contrary, ssDNA were digested and the DNA bands were absent in lanes 4 and 6.

RCA was performed with the circle templates and aptamer-primers. As shown in the 1% agarose gel, RCA products larger than 10 kbp were formed and remained in the loading wells of lanes 2 and 4, corresponding to PDGF-BB circle template/PDGF-BB aptamer-primer and thrombin circle template/thrombin aptamer-primer. Smears of incomplete RCA products of various molecular weights were also formed in these lanes. RCA did not occur when the circle templates were mixed with a non-complementary irrelevant aptamer-primer (lanes 3 and 5), showing specificity of the RCA reaction depending on whether the correct aptamer-primer is present.

Figure 18:
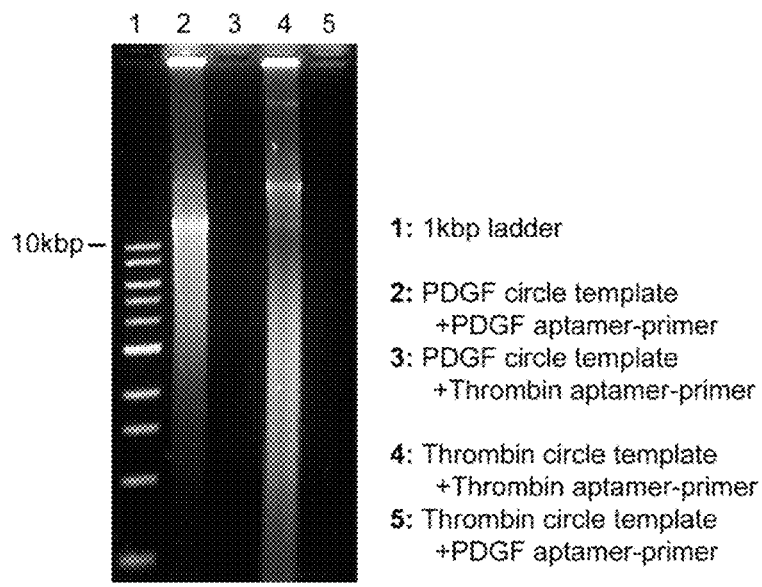
FIG. 18 is a diagram showing a 1% agarose gel. RCA products were formed (DNA product larger than 10 kbp that remained inside the loading wells, and smears of various MW DNA products) when PDGF circle templates were incubated with the PDGF aptamer-primer (lane 2), and when thrombin circle templates were incubated with the thrombin aptamer-primer (lane 4). No RCA products were formed when the circles were incubated with the irrelevant aptamer-primers (lanes 3 and 5).
Figure 19:
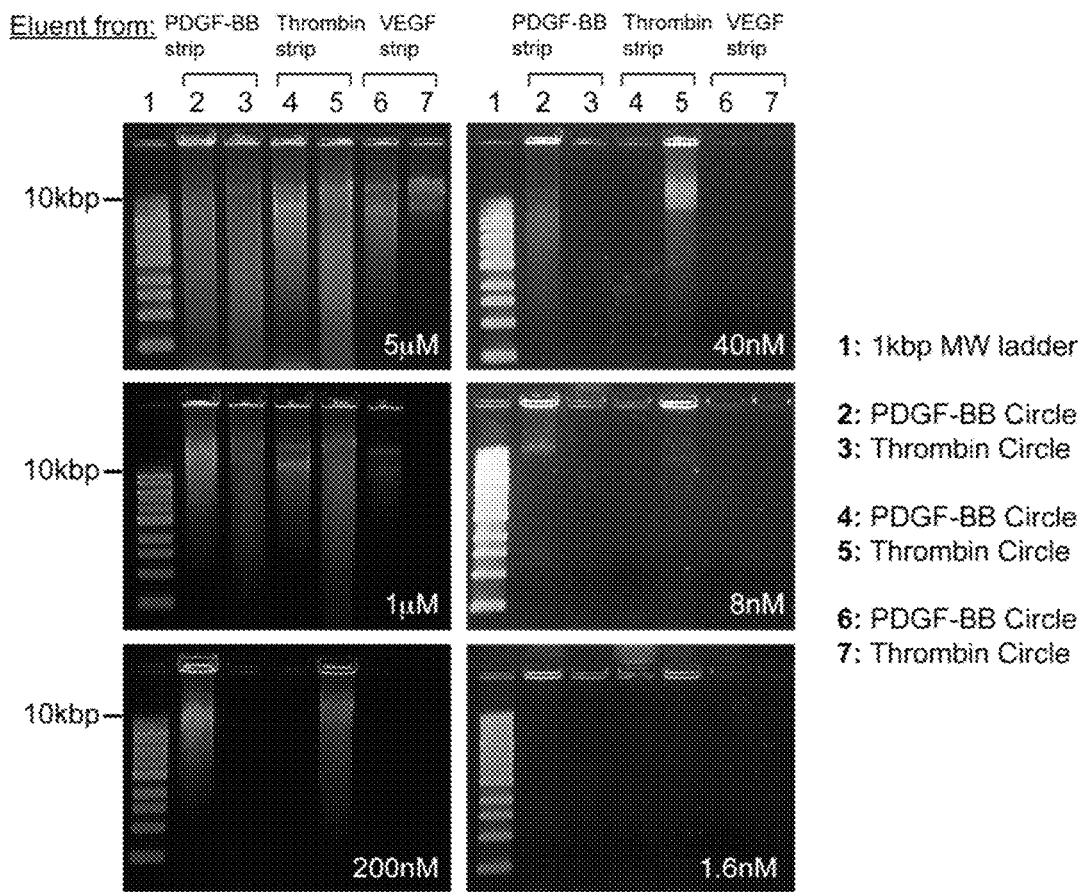
FIG. 19 is a diagram showing a 1% agarose gel. RCA products of PDGF-BB and thrombin aptamer-primers recovered from Peel-Strips immobilized with proteins.

The eluted aptamer-primers from each Peel-Strip were split into two tubes for RCA reactions with PDGF-BB circle template and thrombin circle template. This was performed for each Peel-Strip chip flowed with a different starting concentration of aptamer-primers as described in Table 3 and Table 6. FIG. 18 shows the 1% agarose gels of the RCA reaction products using eluents from the Peel-Strips. At high concentrations of the aptamer-primer mixtures (5 μM and 1 μM) flowed into the microfluidic device, nonspecific binding of the aptamer-primers to the Peel-Strips was abundant and could be seen by the RCA products formed for all lanes 2-7. In the future, more rigorous washing could potentially reduce this nonspecific binding, either by increasing the flow rate or lengthening the washing times. For mixture flowed with a reduced aptamer-primer concentration (200 nM and below), the nonspecific binding of the aptamer-primer to the irrelevant proteins is greatly reduced as seen in FIG. 19. Only lanes 2 and 5 showed RCA products formed as expected, since they are the only RCA reactions containing circle templates with the correct aptamer-primers. As the mixture concentration of aptamer-primers flowed into the microfluidic device decreased, the smears in the lane gradually diminished as less incomplete RCA products were formed. The detection limit of the RCA reaction (stopping at 3 h) is about 1.6 nM of starting aptamer-primers mixture flowed into the microfluidic device. The gel for 1.6 nM aptamer-primers still showed the large RCA products inside the loading wells of lanes 2 and 5 in FIG. 19.

2.14—Conclusions

A simple chip consisting of parylene-A coated Peel-Strips was developed for covalent immobilization of biomolecules (in this example, proteins) to the amine groups on the Peel-Strip surface. Proteins were determined to be functionalized on the surface via fluorescent immunostaining. Furthermore, the bioactivity of one of the proteins (thrombin) was retained after immobilization. The Peel-Strips were then individually spotted and immobilized with a different protein on each strip and incorporated into a microfluidic format for affinity-based screening of aptamers in a mixture binding to the proteins. Afterwards, the Peel-Strips could be mechanically peeled off to recover and elute the bound aptamers for post-screening processing such as DNA amplification. This study is the first demonstration of using parylene-A based Peel-Strips for aptamers separation and recovery. The recovered aptamers were detected by fluorospectrometry and also RCA to verify specific binding to the correct proteins and successful recovery. The limit of detection via the RCA detection scheme is 1.6 nM starting concentration of aptamers flowed into the microfluidic device. Two rounds of SELEX were attempted to enrich and isolate aptamers from a random ssDNA library against three proteins (TNF-, PDGF-BB, and VEGF), but the SELEX process needs to be further optimized. The microfluidic parylene Peel-Strips platform is not limited to screening and recovering aptamers-proteins, but could be generalized to other biomolecular interactions such as protein-protein, protein-cells interactions, nucleic acids hybridization etc. Scaling up may be feasible in the future to high-density smaller strips (e.g. 96-wells format), which can be potentially processed and automated using robotics. This can be extended to other fields such as the screening and selection of rare stem cells, induced pluripotent stem cells etc. Future use of Peel-Strips could also include drug screening for therapeutic aptamers for proteins involved in diseases using SELEX.

REFERENCES

Citation of a reference herein shall not be construed as an admission that such reference is prior art to the present invention. The following references, to the extent that they provide exemplary procedural or other details supplementary to those set forth herein, are specifically incorporated herein by reference:

A1. Y. L. Wang, G. Young, M. Bachman, C. E. Sims, G. P. Li and N. L. Allbritton, Analytical Chemistry, 2007, 79, 2359-2366.
A2. D. Wang, A. Urisman, Y. T. Liu, M. Springer, T. G. Ksiazek, D. D. Erdman, E. R. Mardis, M. Hickenbotham, V. Magrini, J. Eldred, J. P. Latreille, R. K. Wilson, D. Ganem and J. L. DeRisi, Plos Biology, 2003, 1, 257-260.
A3. S. M. Park, J. Y. Ahn, M. Jo, D. K. Lee, J. T. Lis, H. G. Craighead and S. Kim, Lab on a Chip, 2009, 9, 1206-1212.
A4. X. H. Lou, J. R. Qian, Y. Xiao, L. Viel, A. E. Gerdon, E. T. Lagally, P. Atzberger, T. M. Tarasow, A. J. Heeger and H. T. Soh, Proceedings of the National Academy of Sciences of the United States of America, 2009, 106, 2989-2994.
A5. L. C. Harty, M. Garcia-Closas, N. Rothman, Y. A. Reid, M. A. Tucker and P. Hartge, Cancer Epidemiology Biomarkers & Prevention, 2000, 9, 501-506.
A6. J. A. Higgins, M. C. Jenkins, D. R. Shelton, R. Fayer and J. S. Karns, Applied and Environmental Microbiology, 2001, 67, 5321-5324.
A7. A. J. Sigurdson, M. Ha, M. Cosentino, T. Franklin, K. A. Hague, Y. Qi, C. Glaser, Y. Reid, J. B. Vaught and A. W. Bergen, Cancer Epidemiology Biomarkers & Prevention, 2006, 15, 385-388.
A8. K. J. Y. Zhong, C. J. Salas, R. Shafer, A. Gubanov, R. A. Gasser, A. J. Magill, J. R. Forney and K. C. Kain, Journal of Clinical Microbiology, 2001, 39, 1195-1196.
A9. A. J. Chu, Archives of Biochemistry and Biophysics, 2005, 440, 123-132.
A10. C. P. Tan and H. G. Craighead, Materials, 2010, 3, 1803-1832.
A11. C. P. Tan, B. R. Seo, D. J. Brooks, E. M. Chandler, H. G. Craighead and C. Fischbach, Integrative Biology, 2009, 1, 587-594.
A12. C. P. Tan, B. R. Cipriany, D. M. Lin and H. G. Craighead, Nano Letters, 2010, 10, 719-725.
A13. H. Nandivada, H.-Y. Chen, Y. Elkasabi and J. Lahann, in Polymers for Biomedical Applications, American Chemical Society, Washington, D.C., 2008, pp. 283-298.
A14. J. Lahann and R. Langer, Macromolecules, 2002, 35, 4380-4386.
1. Wang, D.; Urisman, A.; Liu, Y. T.; Springer, M.; Ksiazek, T. G.; Erdman, D. D.; Mardis, E. R.; Hickenbotham, M.; Magrini, V.; Eldred, J.; Latreille, J. P.; Wilson, R. K.; Ganem, D.; DeRisi, J. L., Viral discovery and sequence recovery using DNA microarrays. Plos Biology 2003, 1, 257-260.
2. Harty, L. C.; Garcia-Closas, M.; Rothman, N.; Reid, Y. A.; Tucker, M. A.; Hartge, P., Collection of buccal cell DNA using treated cards. Cancer Epidemiology Biomarkers & Prevention 2000, 9, 501-506.
3. Higgins, J. A.; Jenkins, M. C.; Shelton, D. R.; Fayer, R.; Karns, J. S., Rapid extraction of DNA from *escherichia coli* and *cryptosporidium parvum* for use in per. Applied and Environmental Microbiology 2001, 67, 5321-5324.
4. Sigurdson, A. J.; Ha, M.; Cosentino, M.; Franklin, T.; Haque, K. A.; Qi, Y.; Glaser, C.; Reid, Y.; Vaught, J. B.; Bergen, A. W., Long-term storage and recovery of buccal cell DNA from treated cards. Cancer Epidemiology Biomarkers & Prevention 2006, 15, 385-388.
5. Zhong, K. J. Y.; Salas, C. J.; Shafer, R.; Gubanov, A.; Gasser, R. A.; Magill, A. J.; Forney, J. R.; Kain, K. C., Comparison of isocode stix and fta gene guard collection matrices as whole-blood storage and processing devices for diagnosis of malaria by per. Journal of Clinical Microbiology 2001, 39, 1195-1196.
6. Park, S. M.; Ahn, J. Y.; Jo, M.; Lee, D. K.; Lis, J. T.; Craighead, H. G.; Kim, S., Selection and elution of aptamers using nanoporous sol-gel arrays with integrated microheaters. Lab on a Chip 2009, 9, 1206-1212.
7. Lou, X. H.; Qian, J. R.; Xiao, Y.; Viel, L.; Gerdon, A. E.; Lagally, E. T.; Atzberger, P.; Tarasow, T. M.; Heeger, A. J.; Soh, H. T., Micromagnetic selection of aptamers in microfluidic channels. Proceedings of the National Academy of Sciences of the United States of America 2009, 106, 2989-2994.

8. Cho, M.; Xiao, Y.; Nie, J.; Stewart, R.; Csordas, A. T.; Oh, S. S.; Thomson, J. A.; Soh, H. T., Quantitative selection of DNA aptamers through microfluidic selection and high-throughput sequencing. Proceedings of the National Academy of Sciences of the United States of America 2010, 107, 15373-15378.
9. Qian, J. R.; Lou, X. H.; Zhang, Y. T.; Xiao, Y.; Soh, H. T., Generation of highly specific aptamers via micromagnetic selection. Analytical Chemistry 2009, 81, 5490-5495.
10. Tan, C. P.; Craighead, H. G., Surface engineering and patterning using parylene for biological applications. Materials 2010, 3, 1803-1832.
11. Tan, C. P.; Seo, B. R.; Brooks, D. J.; Chandler, E. M.; Craighead, H. G.; Fischbach, C., Parylene peel-off arrays to probe the role of cell-cell interactions in tumour angiogenesis. Integrative Biology 2009, 1, 587-594.
12. Tan, C. P.; Cipriany, B. R.; Lin, D. M.; Craighead, H. G., Nanoscale resolution, multicomponent biomolecular arrays generated by aligned printing with parylene peel-off. Nano Letters 2010, 10, 719-725.
13. Lahann, J.; Pluster, W.; Klee, D.; Gattner, H. G.; Hocker, H., Immobilization of the thrombin inhibitor r-hirudin conserving its biological activity. Journal of Materials Science: Materials in Medicine 2001, 12, 807-810.
14. Nandivada, H.; Chen, H.-Y.; Elkasabi, Y.; Lahann, J., Reactive polymer coatings for biological applications. In Polymers for biomedical applications, American Chemical Society: Washington, D.C., 2008; pp 283-298.
15. Jeon, B. J.; Kim, M. H.; Pyun, J. C., Parylene—a coated microplate for covalent immobilization of proteins and peptides. Journal of Immunological Methods 2010, 353, 44-48.
16. Jeon, B. J.; Kim, M. H.; Pyun, J. C., Application of a functionalized parylene film as a linker layer of spr biosensor. Sensors and Actuators B: Chemical 2010, doi:10.1016/j.snb.2010.1001.1035.
17. Bock, L. C.; Griffin, L. C.; Latham, J. A.; Vermaas, E. H.; Toole, J. J., Selection of single-stranded-DNA molecules that bind and inhibit human thrombin. Nature 1992, 355, 564-566.
18. Zhou, L.; Ou, L. J.; Chu, X.; Shen, G. L.; Yu, R. Q., Aptamer-based rolling circle amplification: A platform for electrochemical detection of protein. Analytical Chemistry 2007, 79, 7492-7500.
19. Potty, A. S. R.; Kourentzi, K.; Fang, H.; Jackson, G. W.; Zhang, X.; Legge, G. B.; Willson, R. C., Biophysical characterization of DNA aptamer interactions with vascular endothelial growth factor. Biopolymers 2009, 91, 145-156.
20. Miwa, J.; Suzuki, Y.; Kasagi, N., Adhesion-based cell sorter with antibody-coated amino-functionalized-parylene surface. Journal of Microelectromechanical Systems 2008, 17, 611-622.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of isolating and recovering a sample biomolecule having affinity to a target component, said method comprising:
   (a) providing a device comprising:
      (i) a support; and
      (ii) at least one peelable layer deposited on at least a portion of the support, wherein said peelable layer comprises a substrate and a target component immobilized on the substrate, wherein said substrate comprises Parylene A or derivatives thereof, wherein said target component comprises a target biomolecule and/or a target biomaterial, and wherein said device is effective for isolating and recovering a biomolecule having affinity to the target component;
   (b) contacting a test sample to the at least one peelable layer under conditions effective to allow a sample biomolecule having affinity to the target component to bind to the target component, thereby isolating the sample biomolecule from the test sample;
   (c) separating the peelable layer containing the isolated sample biomolecule from the support; and
   (d) eluting the isolated sample biomolecule from the peelable layer.

2. The method according to claim 1, wherein the test sample comprises aptamers, proteins, peptides, cells, or mixtures thereof.

3. The method according to claim 1, wherein the target component is immobilized on the substrate by immobilization interactions selected from the group consisting of covalent binding, physical adsorption, and physical steric trapping.

4. The method according to claim 1, wherein the target component is modified to have functional groups effective to facilitate immobilization of the target component to the substrate, said functional groups being selected from the group consisting of hydrophilic groups, hydrophobic groups, carboxyl groups, amine groups, and thiol groups.

5. The method according to claim 1, wherein the substrate comprises surface properties effective for immobilizing the target component thereto, said surface properties being characterized by the presence of functional groups selected from the group consisting of hydrophilic groups, hydrophobic groups, carboxyl groups, amine groups, and gold groups.

6. The method according to claim 1, wherein said support is configured to hold a plurality of peelable layers, wherein each of said peelable layers is independently removable from the support.

7. The method according to claim 1, wherein a plurality of peelable layers are deposited on the support, and wherein each peelable layer comprises either an identical or different target component.

8. The method according to claim 1, wherein said target component comprises said target biomolecule, and wherein the target biomolecule is selected from the group consisting of a protein, a peptide, a nucleic acid molecule, an aptamer, an oligonucleotide, a saccharide, a polysaccharide, a lipid, a glycolipid, a glycoprotein, a cell, and combinations thereof.

9. The method according to claim 1, wherein said target component comprises said target biomaterial, and wherein the target biomaterial is selected from the group consisting of a sol-gel, a hydrogel laden with proteins, a Matrigel, an artificially constructed scaffold with cells, and combinations thereof.

10. The method according to claim 1, wherein the target component has binding affinity to a biomolecule selected from the group consisting of an aptamer, a protein, a peptide, a nucleic acid molecule, an oligonucleotide, a cell-associated molecule, a saccharide, a polysaccharide, a lipid, a glycolipid, a glycoprotein, a cell, and combinations thereof.

11. The method according to claim 1, wherein the target component maintains its bioactivity or functionality.

12. The method according to claim 1, wherein the target component is selected from the group consisting of human TNF-α, human VEGF, human PDGF-BB, human PSA, and human α-Thrombin.

13. The method according to claim 1, wherein said device further comprises:
   a release coating deposited between the support and peelable layer, wherein said release coating is effective to facilitate separation of the peelable layer from the support.

14. The method according to claim 13, wherein said release coating is selected from the group consisting of a detergent/surfactant, bovine serum albumin, and a thin metal layer.

15. The method according to claim 1, wherein the at least one peelable layer further comprises:

a secondary mechanical support layer, wherein said secondary mechanical support layer is deposited between the support and the substrate of the at least one peelable layer, said secondary mechanical support layer being effective to facilitate removal of the peelable layer from the support.

16. The method according to claim 15, wherein said secondary mechanical support layer comprises apara-xylylene polymer selected from the group consisting of Parylene C, Parylene AM, Parylene D, Parylene N, Parylene F, and derivatives thereof.

17. The method according to claim 1, wherein said device further comprises:

a biomolecule bound with affinity to the target component.

18. The method according to claim 1, wherein the device is in the form of a microarray comprising a plurality of peelable layers, and wherein each of the peelable layers is independently removable from the support.

19. The method according to claim 1, wherein the device is effective for multiplexed isolation and recovery of biomolecules from a test sample.

20. A method of isolating and recovering a sample biomolecule having affinity to a target component, said method comprising:

(a) providing a device comprising:
  (i) a support; and
  (ii) at least one peelable layer deposited on at least a portion of the support, wherein said peelable layer comprises a substrate and a secondary mechanical support layer, wherein said substrate has a target component immobilized on the substrate, said target component comprising a target biomolecule and/or a target biomaterial, wherein said secondary mechanical support layer is deposited between the support and the substrate of the at least one peelable layer, wherein said secondary mechanical support layer comprises apara-xylylene polymer selected from the group consisting of Parylene C, Parylene AM, Parylene D, Parylene N, Parylene F, and derivatives thereof, said secondary mechanical support layer being effective to facilitate removal of the peelable layer from the support, and wherein said device is effective for isolating and recovering a biomolecule having affinity to the target component;
(b) contacting a test sample to the at least one peelable layer under conditions effective to allow a sample biomolecule having affinity to the target component to bind to the target component, thereby isolating the sample biomolecule from the test sample;
(c) separating the peelable layer containing the isolated sample biomolecule from the support; and
(d) eluting the isolated sample biomolecule from the peelable layer.

21. The method according to claim 20, wherein said substrate comprises Parylene A or derivatives thereof.

* * * * *

```
                           SEQUENCE LISTING

<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1 ttttttttt ttggttggtg tggttgg                                        27

<210> SEQ ID NO 2
<211> LENGTH: 57
<212> TYPE: DNA
<213> ORGANISM: Artificial Sequence
<220> FEATURE:
<223> OTHER INFORMATION: Primer

<400> SEQUENCE: 2 ttttttttt tttactcagg gcactgcaag caattgtggt cccaatgggc tgagtat       57

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3 ttttttttt ttcccgtctt ccagacaaga gtgcagggg                           39

<210> SEQ ID NO 4
```

```
<211> LENGTH: 53
<212> TYPE: DNA
<213> ORGANISM: Artificial Sequence
<220> FEATURE:
<223> OTHER INFORMATION: Primer

<400> SEQUENCE: 4
aggacacgca ttttactaga tagctagctt tcgatcgttc tgagcagaca acg      53

<210> SEQ ID NO 5
<211> LENGTH: 48
<212> TYPE: DNA
<213> ORGANISM: Artificial Sequence
<220> FEATURE:
<223> OTHER INFORMATION: Primer

<400> SEQUENCE: 5
ggttggtgtg gttggttttt ttttaatgcg tgtcctcgtt gtctgctc             48

<210> SEQ ID NO 6
<211> LENGTH: 80
<212> TYPE: DNA
<213> ORGANISM: Artificial Sequence
<220> FEATURE:
<223> OTHER INFORMATION: Primer

<400> SEQUENCE: 6
tagcacggac atatatgatg gtaccgcagt atgagtatct cctatcacta ctaagtggaa      60
gaaatgtaac tgtttccttc                                                  80

<210> SEQ ID NO 7
<211> LENGTH: 77
<212> TYPE: DNA
<213> ORGANISM: Artificial Sequence
<220> FEATURE:
<223> OTHER INFORMATION: Primer

<400> SEQUENCE: 7
tactcagggc actgcaagca attgtggtcc caatgggctg agtattttt ttgtccgtgc       60 tagaaggaaa cagttac                                                     77

<210> SEQ ID NO 8
<211> LENGTH: 109
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(85)
<223> OTHER INFORMATION: n is a, c, g, or t

<400> SEQUENCE: 8
gggagaattc aactgccatc taggcnnnnn nnnnnnnnnn nnnnnnnnnn nnnnnnnnnn      60
nnnnnnnnnn nnnnnnnnnn nnnnngtact acaagcttct ggactcggt                 109

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
gggagaattc aactgccatc taggc                                            25
```

```
<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
accgagtcca gaagcttgta gtac                                              24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
accgagtcca gaagcttgta gtac                                              24
```